United States Patent
Sintim et al.

(10) Patent No.: US 12,122,786 B2
(45) Date of Patent: Oct. 22, 2024

(54) INHIBITORS OF CYCLIC MONO- AND DI-NUCLEOTIDE PHOSPHODIESTERASES AND THE USES THEREOF

(71) Applicant: Purdue Research Foundation, West Lafayette, IN (US)

(72) Inventors: Herman O. Sintim, West Lafayette, IN (US); George Naclerio, Lafayette, IN (US); Caroline Karanja, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/552,421

(22) Filed: Dec. 16, 2021

(65) Prior Publication Data

US 2022/0194957 A1 Jun. 23, 2022

Related U.S. Application Data

(60) Provisional application No. 63/126,572, filed on Dec. 17, 2020.

(51) Int. Cl.
C07D 495/04 (2006.01)

(52) U.S. Cl.
CPC .................. C07D 495/04 (2013.01)

(58) Field of Classification Search
CPC .......................... C07D 495/04; A61K 31/519
USPC ....................................... 544/278; 514/260.1
See application file for complete search history.

(56) References Cited

U.S. PATENT DOCUMENTS 8,642,660 B2 * 2/2014 Goldfarb .............. A61K 31/122
514/18.9

FOREIGN PATENT DOCUMENTS

WO WO2008147962 * 12/2008 ........... A61K 31/519

OTHER PUBLICATIONS

Wolff et al., "Burger's Medicinal Chemistry and Drug Discovery," 5th Ed. Part 1, pp. 975-977 (1995). (Year: 1995).*
Banker, et al., (1996), Modern Pharmaceuticals, p. 596. (Year: 1996).*
VanDuyne, et al. Journal of Molecular Biology (2013), 425(4), 812-829. (Year: 2013).*
Fahmi, T. et al., c-di-AMP: An Essential Molecule in the Signaling Pathways that Regulate the Viability and Virulence of Gram-Positive Bacteria. Genes 2017, 8 (8), 197; 17 pgs.
Ablasser, A. et al., cGAS produces a 2'-5'-linked cyclic dinucleotide second messenger that activates STING. Nature Jun. 2013, 498 (7454), 380-384.
Lieberman, O. J. et al., High-Throughput Screening Using the Differential Radial Capillary Action of Ligand Assay Identifies Ebselen as an Inhibitor of Diguanylate Cyclases. ACS Chem. Biol. 2014, 9 (1), 183-192.
Sambanthamoorthy, K. et al., Identification of small molecules inhibiting diguanylate cyclases to control bacterial biofilm development. Biofouling 2014, 30 (1), 17-28.
Zheng, Y. et al., Identification of bromophenol thiohydantoin as an inhibitor of DisA, a c-di-AMP synthase, from a 1000 compound library, using the coralyne assay. Chem. Commun. 2014, 50 (76), 11234-11237.
Opoku-Temeng, C. et al., Potent inhibition of cyclic diadenylate monophosphate cyclase by the antiparasitic drug, suramin. Chem. Commun. 2016, 52 (19), 3754-3757.
Opoku-Temeng, C. et al., Inhibition of cyclic diadenylate cyclase, DisA, by polyphenols. Sci. Rep. 2016, 6, 25445-25445, 1-8.
Opoku-Temeng, C. et al., Hydroxybenzylidene-indolinones, c-di-AMP synthase inhibitors, have antibacterial and anti-biofilm activities and also re-sensitize resistant bacteria to methicillin and vancomycin. RSC Advances 2017, 7 (14), 8288-8294.
Dey, R. J. et al., Inhibition of innate immune cytosolic surveillance by an M. tuberculosis phosphodiesterase. Nat. Chem. Biol. 2017, 13 (2), 210-217 (published online Dec. 12, 2016).
Zheng, Y. et al., Inhibition of P. aeruginosa c-di-GMP phosphodiesterase RocR and swarming motility by a benzoisothiazolinone derivative. Chem. Sci. 2016, 7 (9), 6238-6244.
Man, H.-W. et al., Discovery of (S)-N-{2-[1-(3-Ethoxy-4-methoxyphenyl)-2-methanesulfonylethyl]-1,3-dioxo-2,3-dihydro-1H-isoindol-4-yl}acetamide (Apremilast), a Potent and Orally Active Phosphodiesterase 4 and Tumor Necrosis Factor-α Inhibitor. J. Med. Chem. 2009, 52 (6), 1522-1524.
Wang, Z. et al., The selectivity and potency of the new PDE5 inhibitor TPN729MA. J. Sex. Med. 2013, 10 (11), 2790-2797.

* cited by examiner

*Primary Examiner* — Jeffrey H Murray
(74) *Attorney, Agent, or Firm* — Purdue Research Foundation

(57) ABSTRACT

The described compounds are of the class of cyclic nucleotides, both mono- and di-nucleotides, which play diverse roles in the prokaryotes and eukaryotes having the general formula

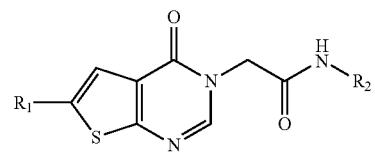

which inhibit phosphodiesterases that inhibit cyclic mono-nucleotide or dinucleotides and/or both mononucleotide and dinucleotide. These compounds have potential diverse applications as antiviral, antibacterial, anti-inflammatory and anticancer agents, including cancer immunotherapy. Pharmaceutical compositions and methods for treating those kinase related diseases are within the scope of this invention.

6 Claims, 10 Drawing Sheets

Enoximone

Sildenafil

Apremilast

Papaverine

ENPP1 Inhibitor C

Compound 1

3 Hours Incubation

Overnight Incubation

INHIBITORS OF CYCLIC MONO- AND DI-NUCLEOTIDE PHOSPHODIESTERASES AND THE USES THEREOF

CROSS-REFERENCE TO RELATED APPLICATIONS

The present U.S. patent application relates to and claims the priority benefit of U.S. Provisional Patent Application Ser. No. 63/126,572, filed Dec. 17, 2020, the contents of which are hereby incorporated by reference in its entirety into this disclosure.

TECHNICAL FIELD

The present disclosure generally relates to series inhibitors of cyclic mono-nucleotide and cyclic dinucleotide phosphodiesterases and methods of uses thereof.

BACKGROUND

This section introduces aspects that may help facilitate a better understanding of the disclosure. Accordingly, these statements are to be read in this light and are not to be understood as admissions about what is or is not prior art.

Immune cells sense bacterial-derived c-di-GMP and c-di-AMP as well as host-derived cGAMP, which is synthesized by cGAS upon binding to pathogen's DNA, to mount immunological response (cytokine production) via the STING-TBK1 pathway. Successful pathogens, such as *Mycobacterium tuberculosis* and group B *streptococcus* harbor phosphodiesterases (PDEs) that can cleave bacterial c-di-AMP as well as host-derived cGAMP to blunt host's response to infection. Selective inhibitors of bacterial cyclic dinucleotide (CDN) PDEs are needed as tool compounds to study the role(s) of CDN PDEs during infection and they could also become bona fide antivirulence compounds, antibacterial, anti-inflammatory, as well as anticancer agents, but there is a paucity of such compounds. There are unmet medical needs.

BRIEF DESCRIPTION OF DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 1A: Schematic illustration of c-di-AMP and cGAMP induction of type I interferon response via the STING pathway and attenuation of this response by MTB CdnP phosphodiesterase (CdnP) inside a macrophage. FIG. 1B: Inhibitors of cyclic mononucleotide PDEs. FIG. 1C: Inhibitors of cyclic dinucleotide PDEs. ENPP1 IC50=260 nM 8. IC50s of the commercial PDEs inhibitors indicated in the text.

FIG. 4A: Coralyne assay profiles of MTB CdnP c-di-AMP hydrolysis in the presence of C14, C40, and C86 molecules. FIG. 4B: Coralyne assay profiles of MTB CdnP c-di-AMP hydrolysis in the presence of C16, C85, and C82 molecules. * Assay parameters: 10 µM compounds, 0.5 µM MTB CdnP, 10 µM, 10 mM KI, reaction buffer (50 mM Tris-HCl pH 8.0, 5 mM $MnCl_2$). Experiment conducted in triplicates at 30° C.

FIG. 5A) HPLC profiles of C-di-AMP cleavage by MTB CndP in the absence and presence of inhibitors after 3 h incubation. FIG. 5B: HPLC profiles of C-di-AMP cleavage by MTB CndP in the absence and presence of inhibitors after 12 h incubation. Experiment conducted with 100 nM MTB CdnP, 70 µM c-di-AMP in 1× reaction buffer (50 mM Tris-HCl pH 8.0, 5 mM $MnCl_2$), incubated at 37° C. for indicated duration. Reactions analyzed with COSMOSIL C18-MS-II column.

FIG. 7A: unlabeled c-di-AMP inhibits $^{32}$P-c-di-AMP sequestering by MTB CdnP in a concentration dependent manner. FIG. 7B: C82 effects on $^{32}$P-c-di-AMP sequestering by MTB CdnP. Experiments (a, and b) conducted with 20 µM MTB CdnP, 1× reaction buffer (50 mM Tris-HCl, pH=7.5, 5 mM calcium chloride), and 200 pM $^{32}$P c-di-AMP. FIG. 7C: C-di-AMP significantly attenuates fluorescent c-di-GMP anisotropy in a concentration dependent manner. FIG. 7D: C82 does not attenuate fluorescent c-di-GMP anisotropy. Experiments (c, and d) conducted with 150 µM MTB CdnP, 1× reaction buffer (50 mM Tris-HCl, pH=7.5, 5 mM calcium chloride), and 50 nM F-c-di-GMP. CDA=c-di-AMP. ***=p-value<0.001. Statistical analysis conducted using the student's t-test.

DETAILED DESCRIPTION

Figure 1A:
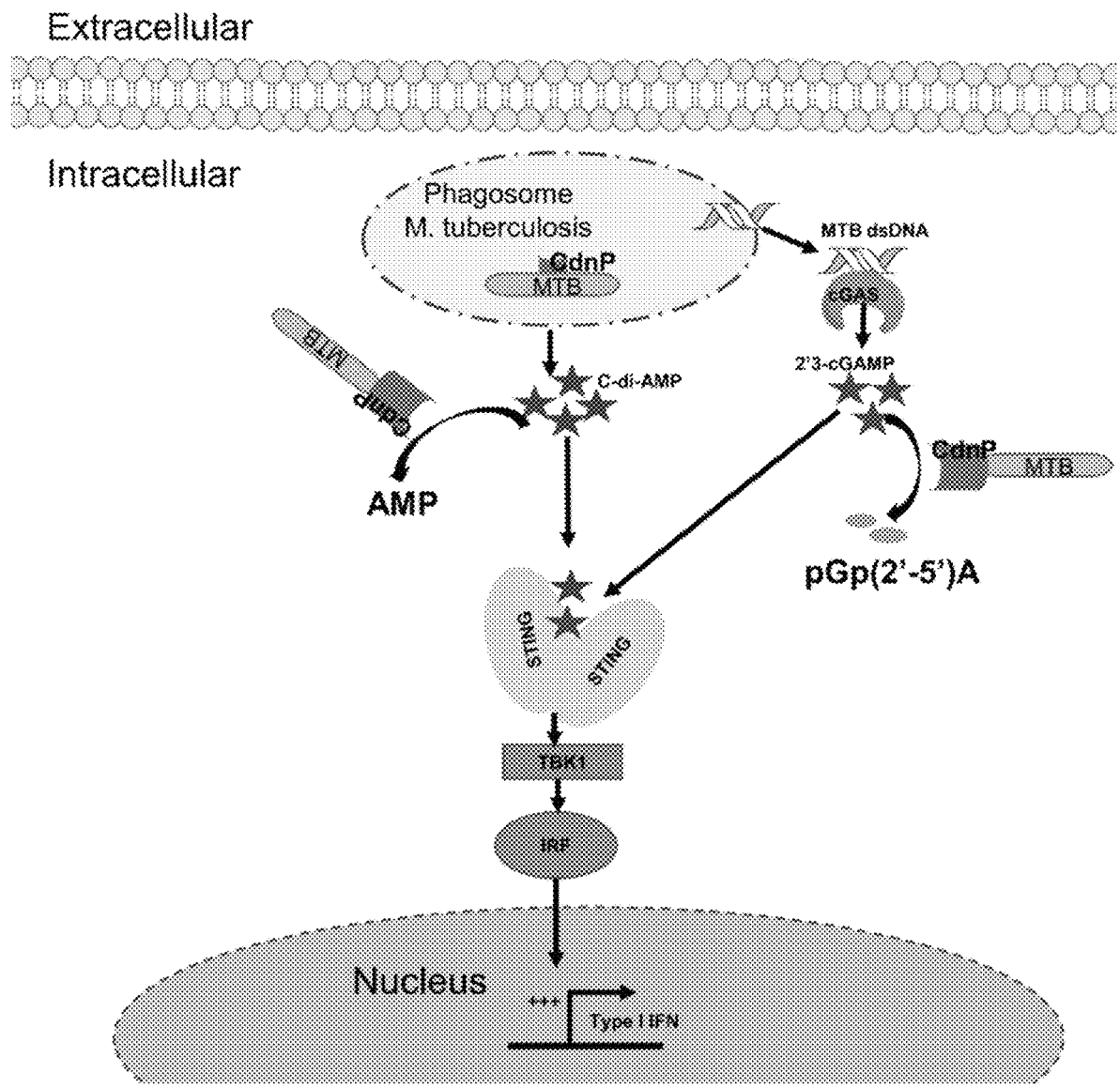
FIGS. 1A-1C: MTB CdnP phosphodiesterase activity inside a macrophage and structures of PDEs inhibitors.

While the concepts of the present disclosure are illustrated and described in detail in the description herein, results in the description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C (CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a mono alkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, this disclosure relates to a compound of a generic structure,

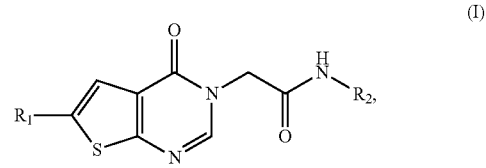

or a pharmaceutically acceptable salt thereof, wherein
$R_1$ is a hydrogen, halo, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and
$R_2$ is an alkyl, alkyloxy, alkylamino, alkenyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted.

In some illustrative embodiments, this disclosure relates to a compound of a generic structure (I), wherein $R_2$ is an alkyl or a cycloalkyl.

In some illustrative embodiments, this disclosure relates to a compound of a generic structure (I), wherein $R_2$ is an aryl, a heteroaryl, or an arylalkyl (alkyl aryl).

In some illustrative embodiments, this disclosure relates to a compound of a generic structure (II),

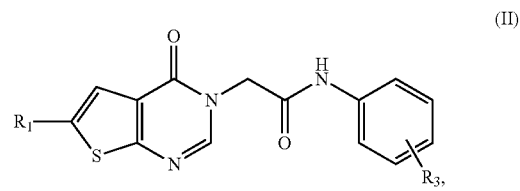

wherein
$R_1$ is a hydrogen, halo, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and
$R_3$ represents five substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety.

In some illustrative embodiments, this disclosure relates to a compound of a generic structure (I), wherein said compound has a formula of
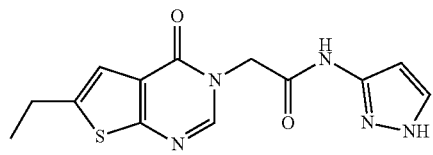
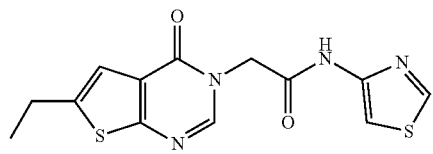
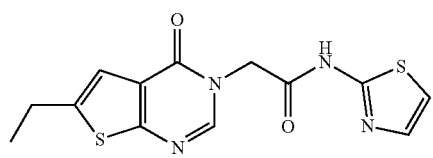
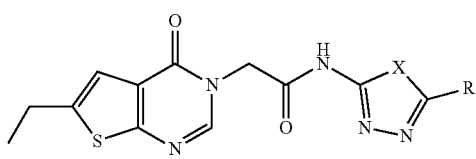
X = O, S, NR
R = Me, CF₃ or Ph
or thiophene
HSDP-15
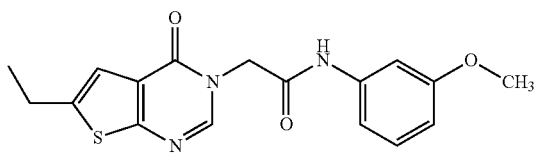 [SMILES: CCc1cc2c(=O)n(CC(=O)Nc3cccc(OC)c3)cnc2s1]
HSDP-16
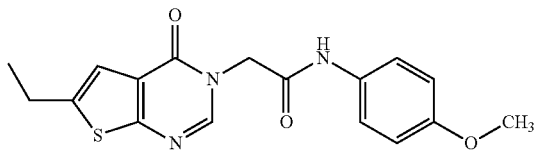
HSDP-17
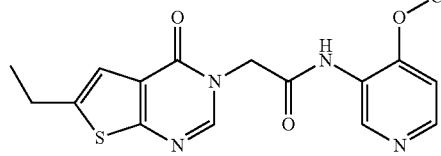
HSDP-18
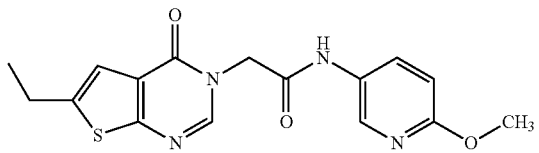
HSDP-20
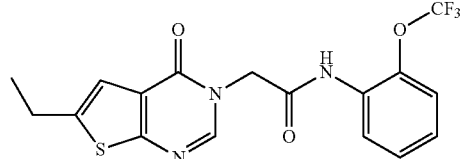
HSDP-23
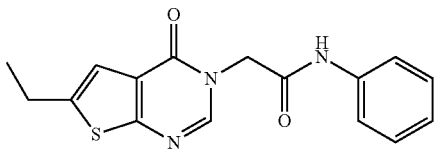
HSDP-24
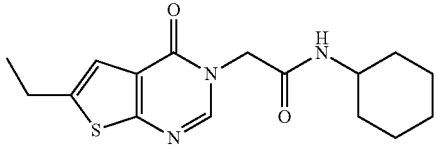
HSDP-25
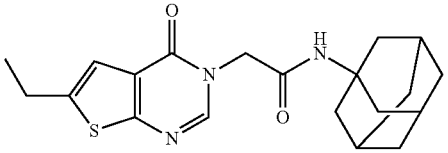
HSDP-26
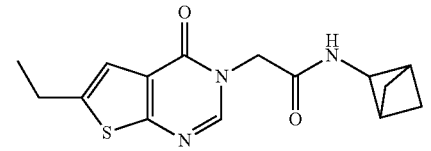
HSDP-27
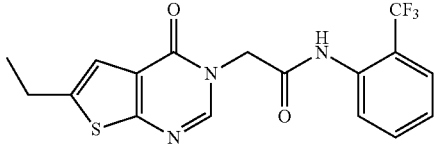
HSDP-28
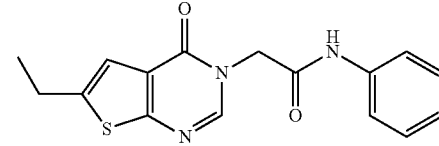
HSDP-29
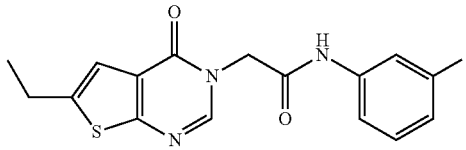
HSDP-30
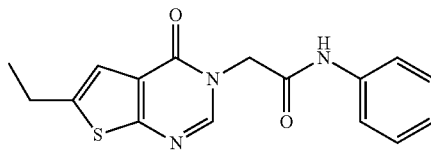

HSDP-31
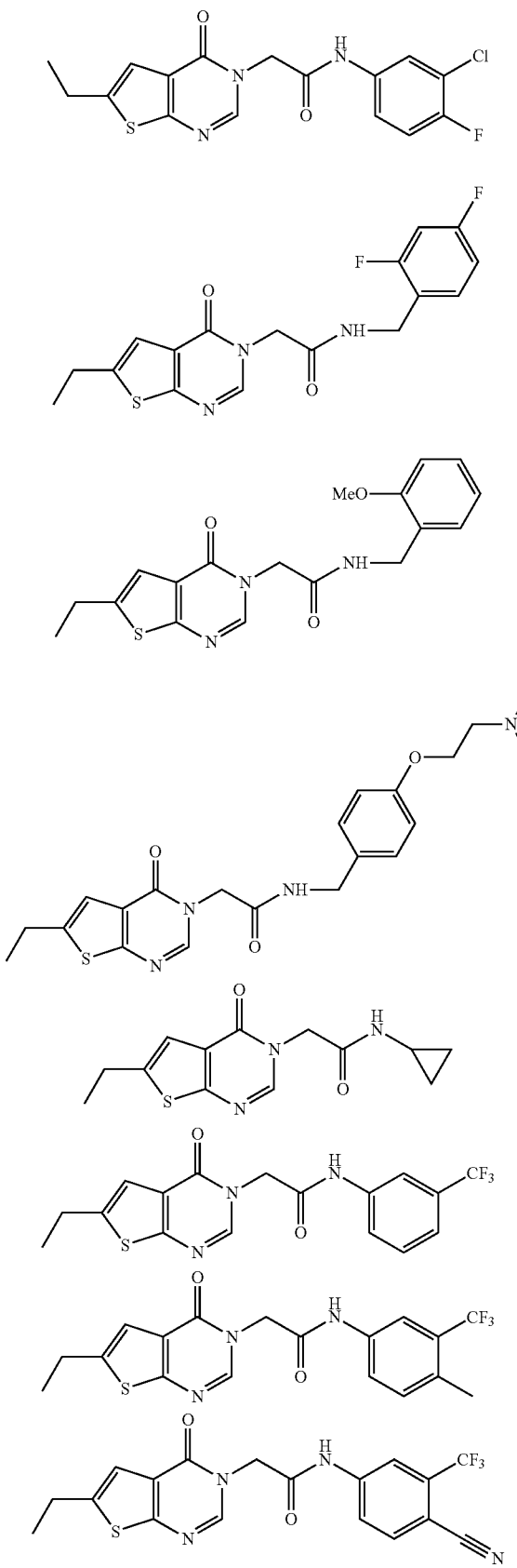
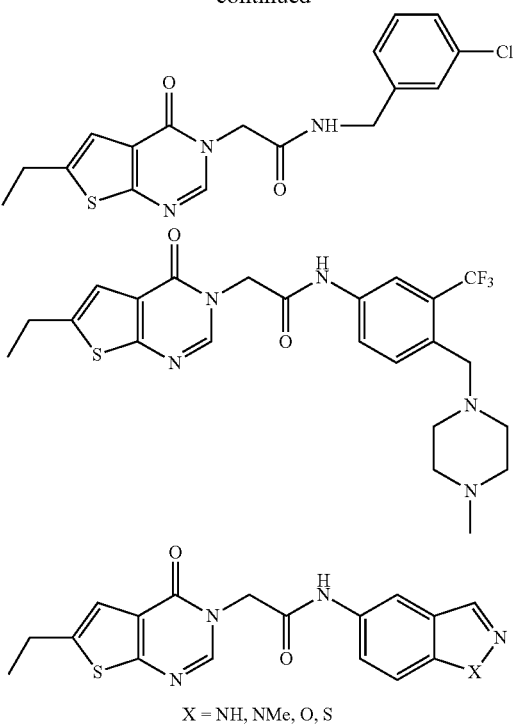
X = NH, NMe, O, S
R = H, Me, CF₃; X = N or S or O

-continued

HSGN-0401
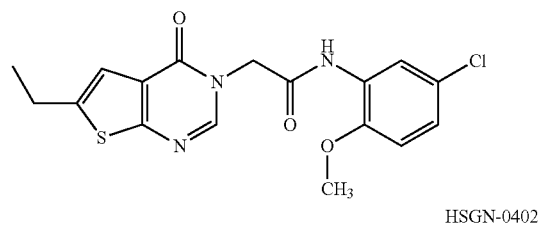

HSGN-0402
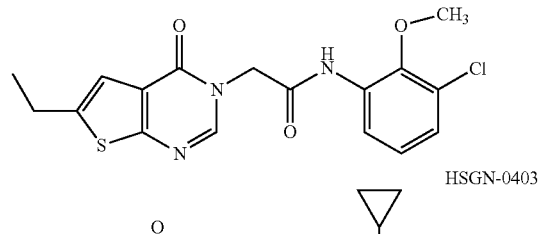

HSGN-0403
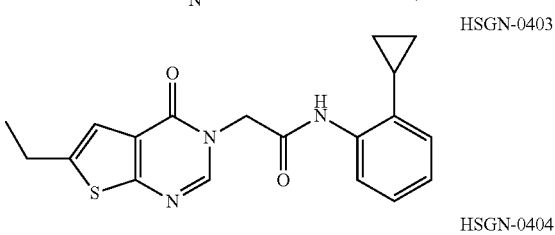

HSGN-0404
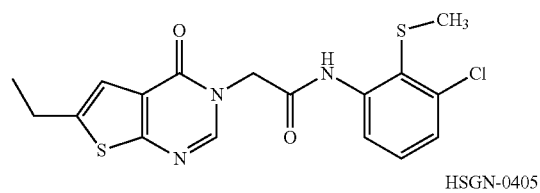

HSGN-0405
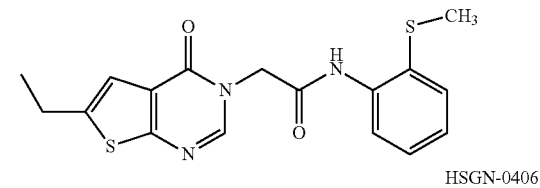

HSGN-0406
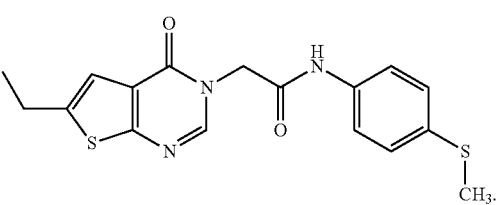

In some illustrative embodiments, this disclosure relates to a compound of a generic structure (I), wherein said compound is an inhibitor for cyclic mononucleotide or cyclic dinucleotide PDE.

In some illustrative embodiments, this disclosure relates to a pharmaceutical composition comprising one or more compounds as disclosed herein, together with one or more pharmaceutically acceptable carriers or diluents.

In some illustrative embodiments, this disclosure relates to a method for treating an infection disease in a subject in need thereof, wherein the method comprises administering to the subject a therapeutically effective amount of one or more compounds as disclosed herein.

In some illustrative embodiments, this disclosure relates to a method for treating an infection disease in a subject in need thereof, wherein said method, for treating a disease of viral infection in a subject in need thereof, comprises administering to the subject a therapeutically effective amount of one or more compounds as disclosed herein.

In some illustrative embodiments, this disclosure relates to a method for treating an inflammatory disease in a subject in need thereof, wherein the method comprises administering to the subject a therapeutically effective amount of one or more compounds as disclosed herein.

In some illustrative embodiments, this disclosure relates to a bifunctional conjugate, wherein one of the functional moiety is a compound as disclosed herein, which is linked to a degrader, such as Protac, or a targeting agent, such as an antibody or small molecule or peptide that binds to a surface receptor to internalize the active ligand.

In some illustrative embodiments, this disclosure relates to a prodrug of a compound as disclosed herein, wherein said prodrug is acid sensitive or reactive to an enzyme.

In some other illustrative embodiments, this disclosure relates to a method for treating an infection disease in a subject in need thereof, wherein the method comprises administering to the subject a therapeutically effective amount of an inhibitor for cyclic mononucleotide or cyclic dinucleotide PDE having a generic structure (I),

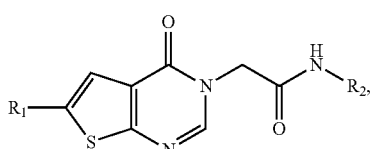
(I)

or a pharmaceutically acceptable salt thereof, wherein
$R_1$ is a hydrogen, halo, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and
$R_2$ is an alkyl, alkyloxy, alkylamino, alkenyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted.

In some other illustrative embodiments, this disclosure relates to a method for treating an infection disease in a subject in need thereof, wherein $R_2$ is an alkyl or a cycloalkyl.

In some other illustrative embodiments, this disclosure relates to a method for treating an infection disease in a subject in need thereof, wherein $R_2$ is an aryl, a heteroaryl, or an arylalkyl (alkyl aryl).

Yet in some other illustrative embodiments, this disclosure relates to a method for treating an infection disease in a subject in need thereof, wherein said compound has a generic structure (II)

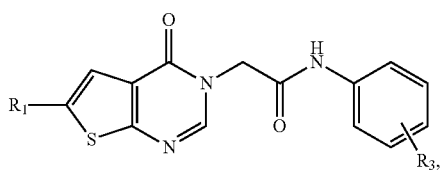
(II)

or a pharmaceutically acceptable salt thereof, wherein

R₁ is a hydrogen, halo, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and R₃ represents five substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety.

In some illustrative embodiments, this disclosure relates to a method for treating an infection disease in a subject in need thereof, wherein said compound has a formula of

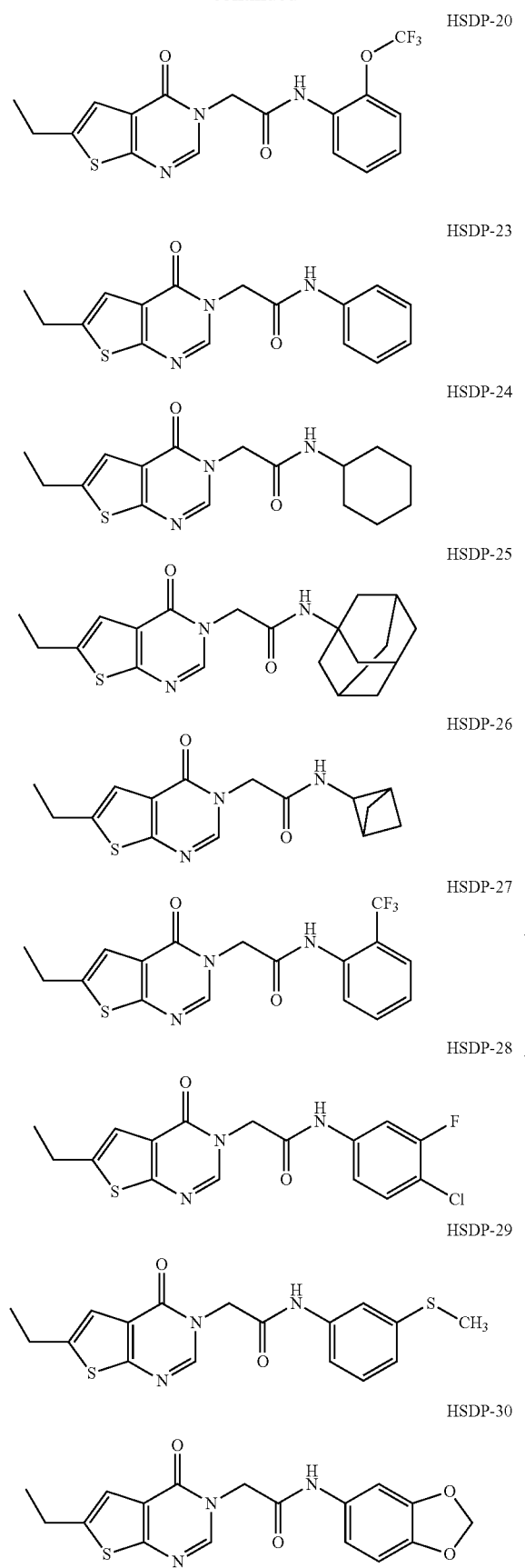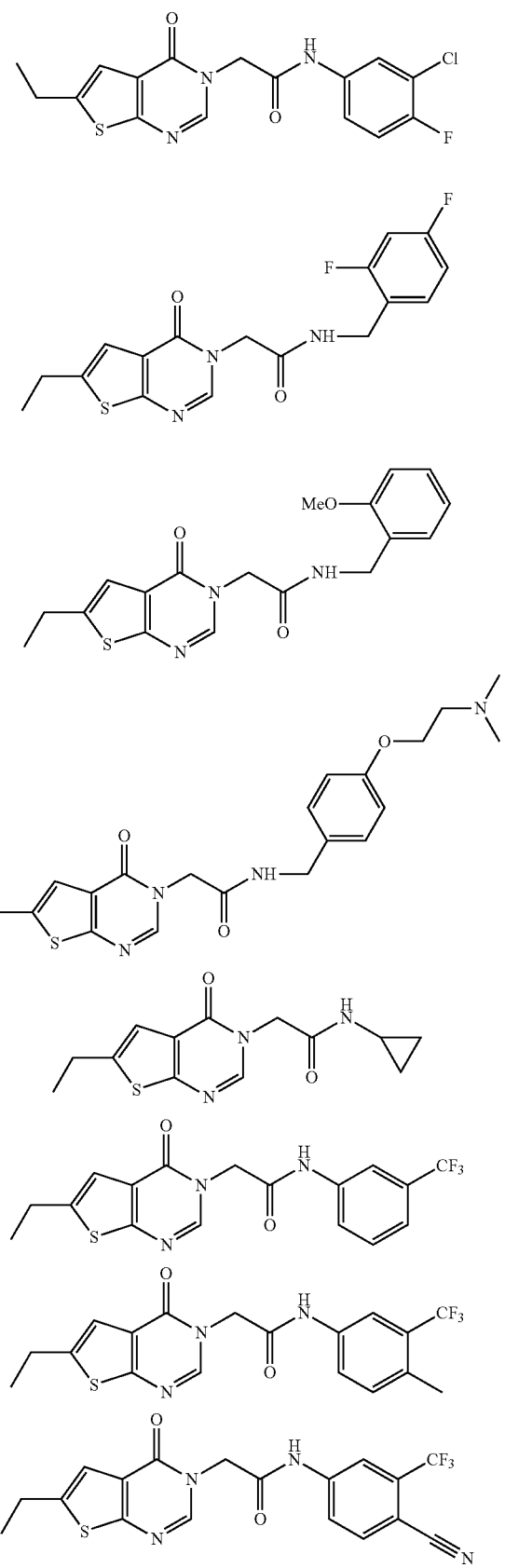

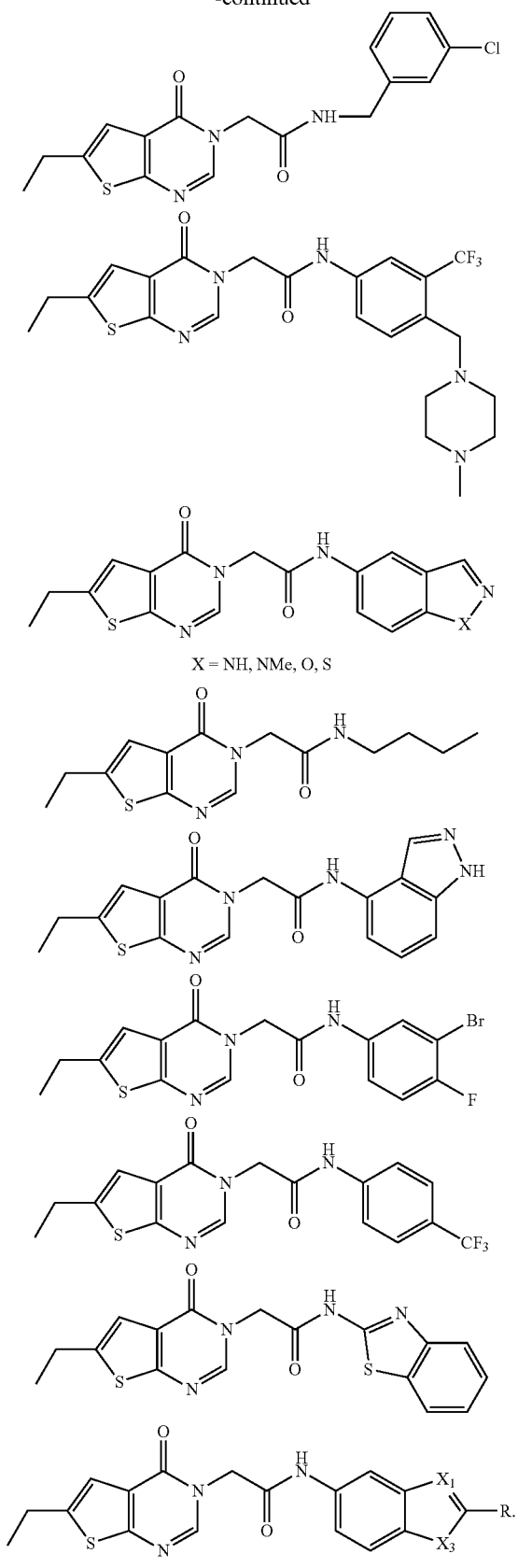

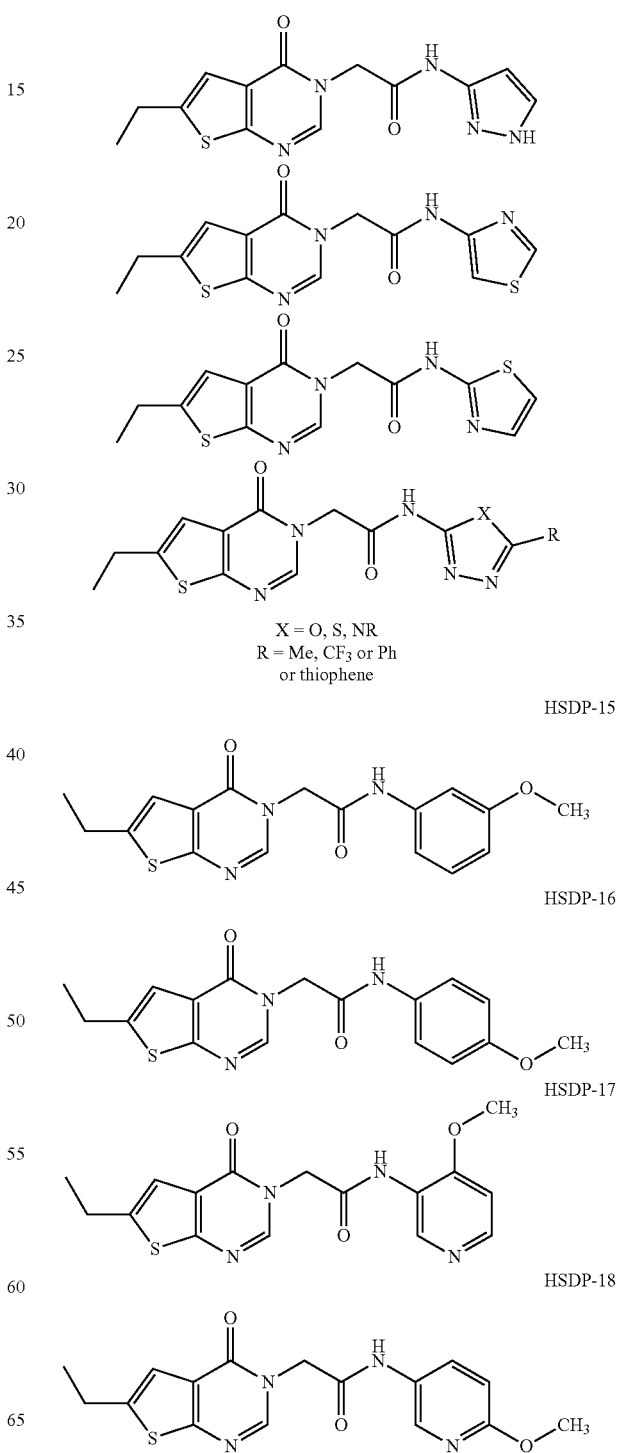

Yet in some other illustrative embodiments, this disclosure relates to a pharmaceutical composition of a compound as disclosed herein for the treatment of an infection disease caused by a bacteria or a virus.

Yet in some other illustrative embodiments, this disclosure relates to an inhibitor for cyclic mononucleotide or cyclic dinucleotide PDE comprising a compound having the formula, an analog thereof, or a pharmaceutically acceptable salt thereof:

-continued
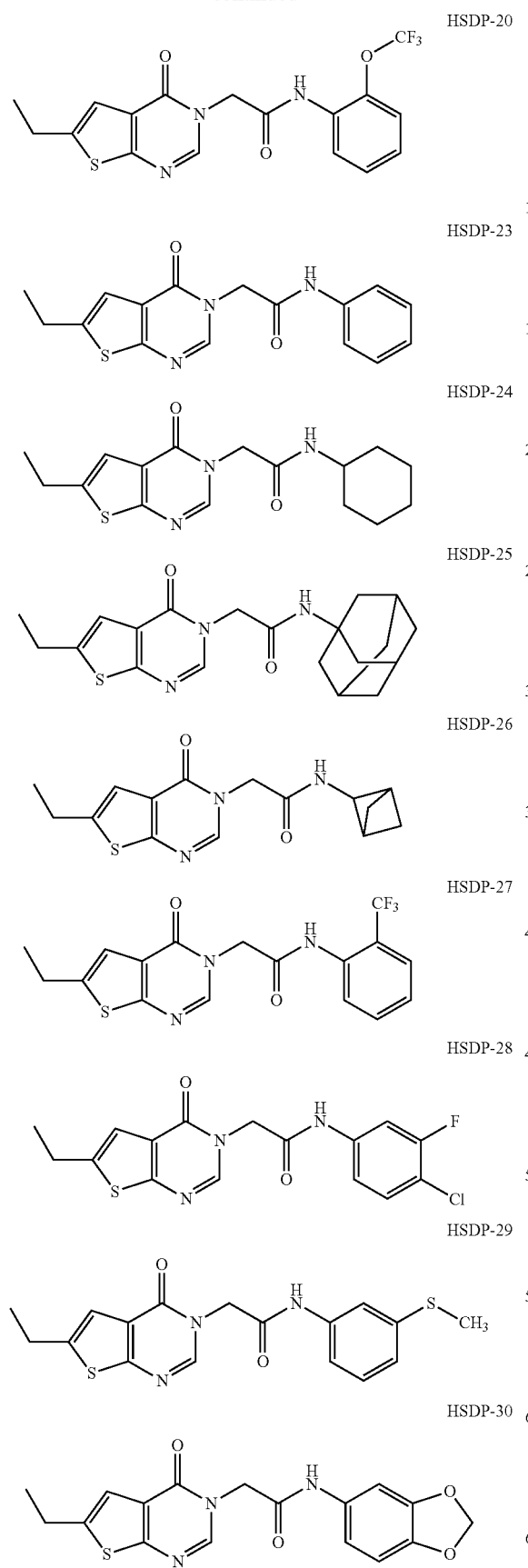
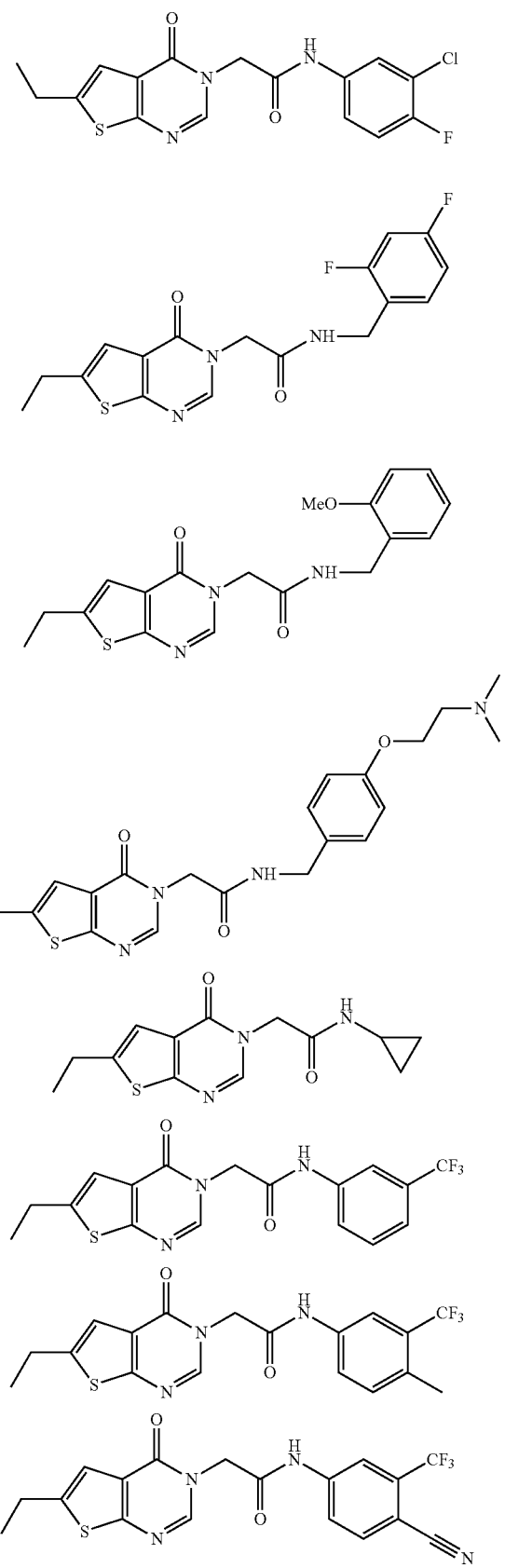

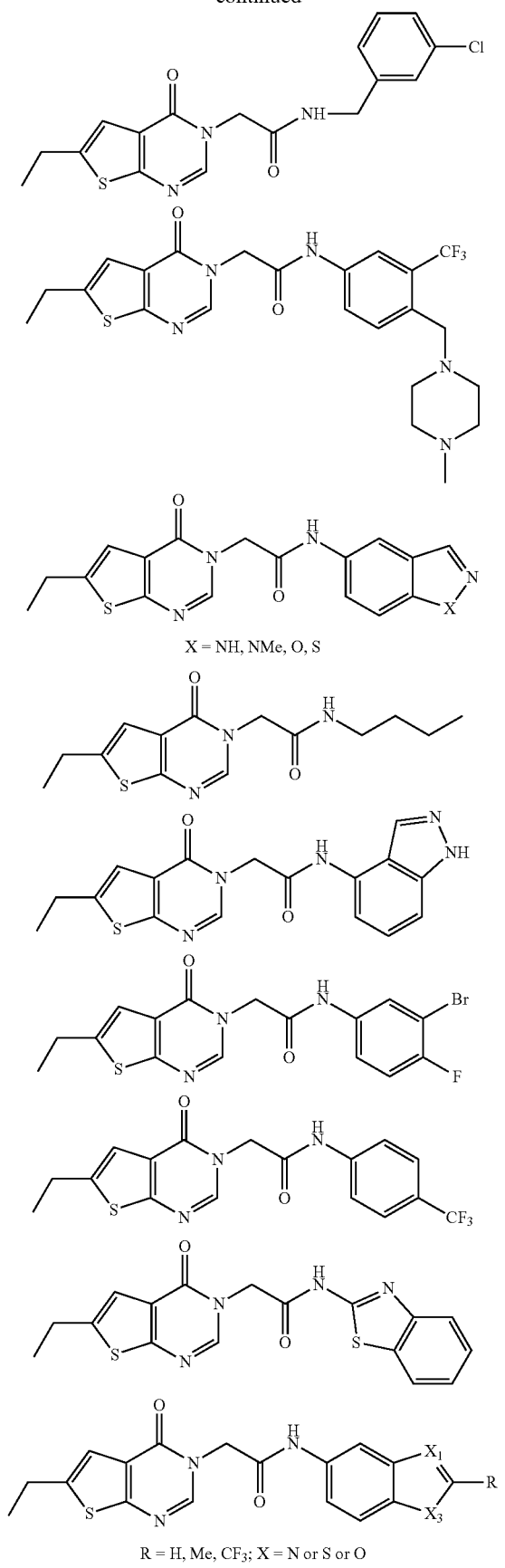

X = NH, NMe, O, S

R = H, Me, CF₃; X = N or S or O

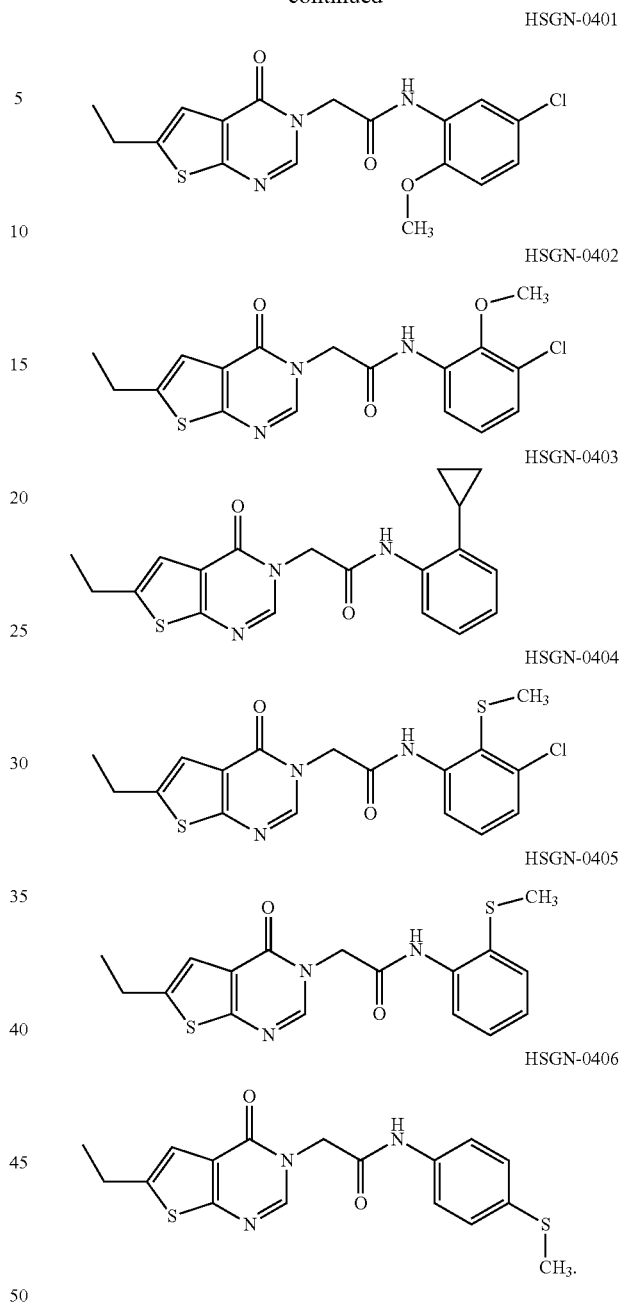

Cyclic dinucleotides (CDNs) have emerged as important second messengers that regulate a dizzying array of processes in all kingdoms. In bacteria, c-di-GMP, c-di-AMP and 3'3'-cGAMP have been shown to regulate different aspects of bacterial physiology, ranging from biofilm formation, and antibiotic resistance to adaptation to different environmental conditions[1]. CDNs cellular levels are maintained by CDN synthesizing enzymes (diadenylate cyclase for c-di-AMP, diguanylate cyclase for c-di-GMP and cGAMP synthase for 3'3'-cGAMP) and degrading enzymes phosphodiesterase (PDEs). Metazoans also make cyclic dinucleotides, such as 2'3'-cGAMP (which contains one non-canonical 2'5'-phosphodiester linkage)[2]. 2'3'-cGAMP (referred to as cGAMP hereafter), synthesized by cyclic GMP-AMP synthase (cGAS), is an immune function regulator that signals via the STING-TBK1 pathway[3]. Bacterial-derived cyclic dinucleotides also activate the STING pathway and hence immune cells are able to sense the presence of intracellular bacteria by either making their own cGAMP upon sensing bacterial DNA in the cytosol or via the binding of bacterial cyclic dinucleotides to STING[4]. Due to the vital role that CDNs play in bacterial physiology and the innate immune system, bacterial CDN synthesizing and degrading enzymes have been targeted for the development of therapeutic agents.

Diguanylate cyclase inhibitors with antibiofilm properties have been reported[5]. Several diadenylate cyclase inhibitors, which have antibacterial properties and also potentiate existing traditional antibiotics, have been identified as well[6]. Our group was the first to report a diadenylate cyclase inhibitor with antibacterial and antibiofilm activity[7]. In contrast to the many reported c-di-GMP or c-di-AMP synthase inhibitors, which have been reported, there is a paucity of identified bacterial CDN phosphodiesterase (PDE) inhibitors.

Cyclic-di-AMP is essential for many human pathogens (mainly Gram positive bacteria and mycobacteria) as it regulates key processes, such as osmoregulation[1b,9]. For intracellular bacteria, especially those that infect phagocytic cells (such as MTB), the release of bacterial-derived c-di-AMP into the host's cytosol can also elicit host's immune response via the STING-TBK1 pathway to facilitate pathogen clearance. Successful pathogens, such as MTB and group B streptococcus (which can also exist intracellularly) have developed sophisticated systems to evade regulation whiles inside phagocytic cells[10]. MTB harbors a c-di-AMP phosphodiesterase (CdnP) that not only hydrolyzes bacterial derived c-di-AMP to attenuate activation of STING but also modulates host-derived cGAMP; the mechanism via which MTB CdnP gains access to the host's cGAMP is known[10a] (FIG. 1a). An analogous pathogen attenuation of host signaling has also been described in group B streptococcus whereby bacterial cyclic dinucleotide phosphodiesterase (membrane anchored and extracellular) degrades any c-di-AMP that is secreted out of the bacteria, thereby reducing the pathogen associated molecular pattern (PAMP) level that could be sensed by the host[10b]. Recently, it was disclosed that certain viruses also harbor cyclic dinucleotide phosphodiesterases (such as poxins), which degrade host cGAMP[11]. Thus it is appearing that one of the major ways that pathogens circumvent immune response is to disable the host's STING signaling response. Consequently, selective cyclic dinucleotide phosphodiesterase inhibitors are needed as tool compounds to decipher the roles of various cyclic dinucleotide phosphodiesterases in bacterial and immune cell physiology. Additionally these compounds could be developed into antivirulence and/or immune adjuvants or boosters. It is crucial that selective CdnP inhibitors are developed to avoid perturbing the dynamics of commensal or resident bacteria.

Figure 1B:
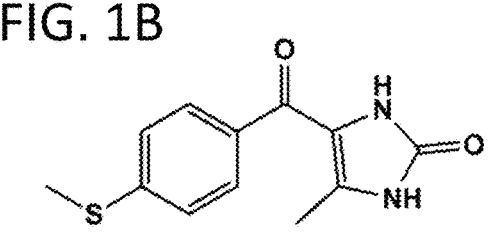
Figure 1B:
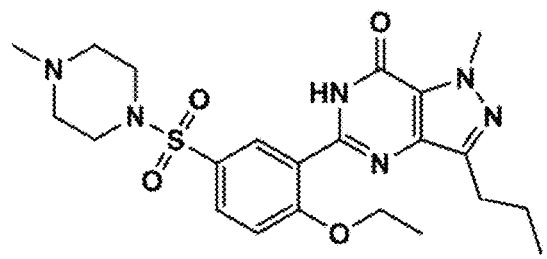
Figure 1B:
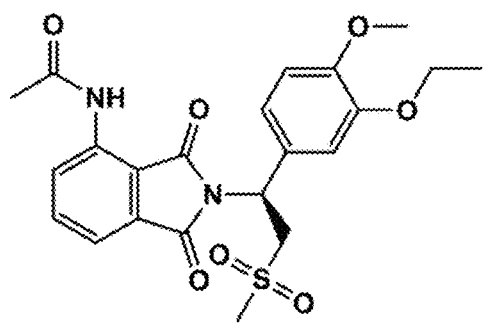
Figure 1B:
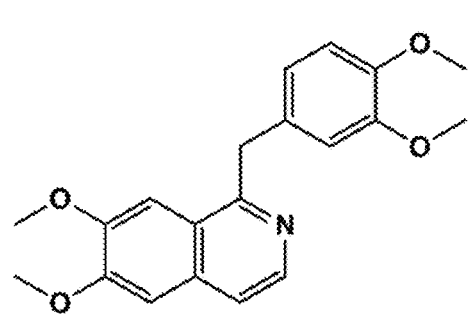
Figure 1C:
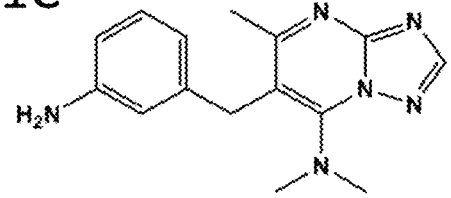
Figure 1C:
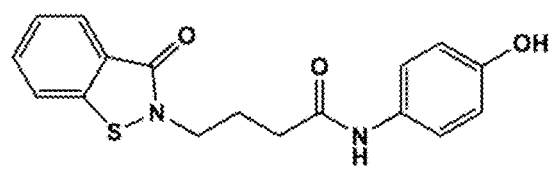

Many compounds that inhibit mammalian cGMP or cAMP PDEs have been developed and some are used in the clinic for diverse diseased states, such as cardiac failure (example is PDE3 inhibitor enoximone, half maximal inhibitory concentration ($IC_{50}$)=10 $\mu M^{12}$), psoriatic arthritics (example is PDE4 inhibitor apremilast, $IC_{50}$=74 $nM^{13}$), erectile dysfunction (example is PDE5 inhibitor sildenafil, $IC_{50}$=5.22 $nM^{14}$) and vasospasm (example is PDE10 inhibitor papaverine, $IC_{50}$=92.3 $nM^{15}$), see FIG. 1b for structures of PDE inhibitors. As stated earlier, only a handful of compounds that inhibit cyclic dinucleotide phosphodiesterases (for few reported examples, see FIG. 1c) have been reported, although it is emerging that these enzymes could also play important roles in various disease progressions[8,16]. The Sintim group reported a benzoisothiazolinone derivative (Compound 1) as a selective inhibitor of c-di-GMP PDE RocR[16a]. This compound could inhibit swarming motility in Pseudomonas aeruginosa. In another report, the Sintim group also reported that linear dinucleotides with hydrolysis resistant phosphodiester linkages could inhibit MTB CdnP, a virulence factor[10a]. A major limitation of these linear dinucleotide analogs is poor cell permeation. Herein, we disclose the identification of a selective non nucleotide-based MTB CdnP inhibitor, which does not inhibit cyclic dinucleotide PDEs from other bacteria. Consequently, this compound or analogs thereof could be used as tool compounds to provide insights into how MTB CdnP regulates various aspects of infection and may even be developed into antivirulence MTB therapeutics.

Figure 2:
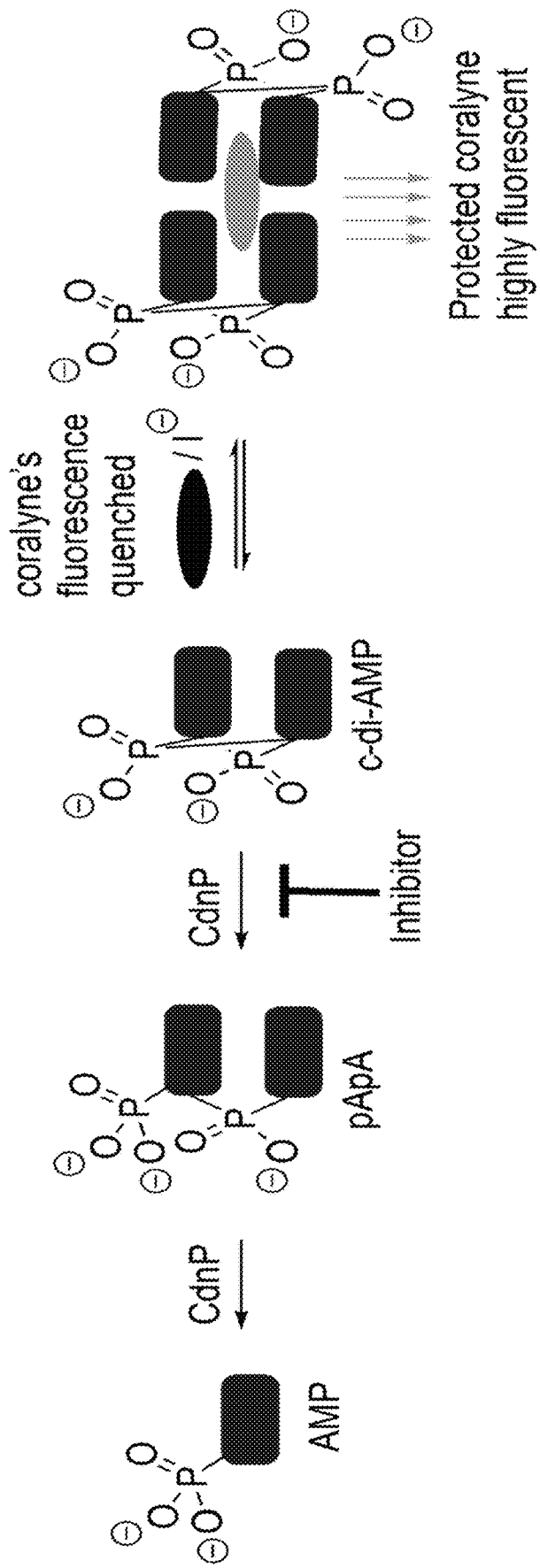
FIG. 2: Monitoring of c-di-AMP hydrolysis by MTB CdnP with the coralyne assay. C-di-AMP forms a complex with coralyne resulting in coralyne fluorescence enhancement. MTB CdnP hydrolyzes c-di-AMP into two molecules of AMP (only one is shown in figure), which does not enhance coralyne fluorescence.
Figure 3:
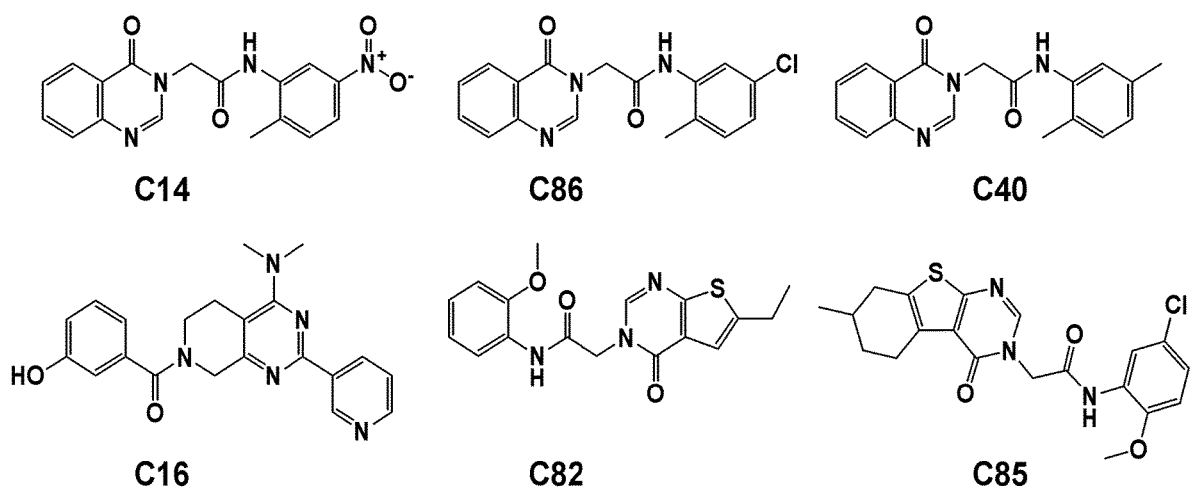
FIG. 3: Structures of inhibitors of MTB CdnP, which were identified from the HTS.
Figure 4A:
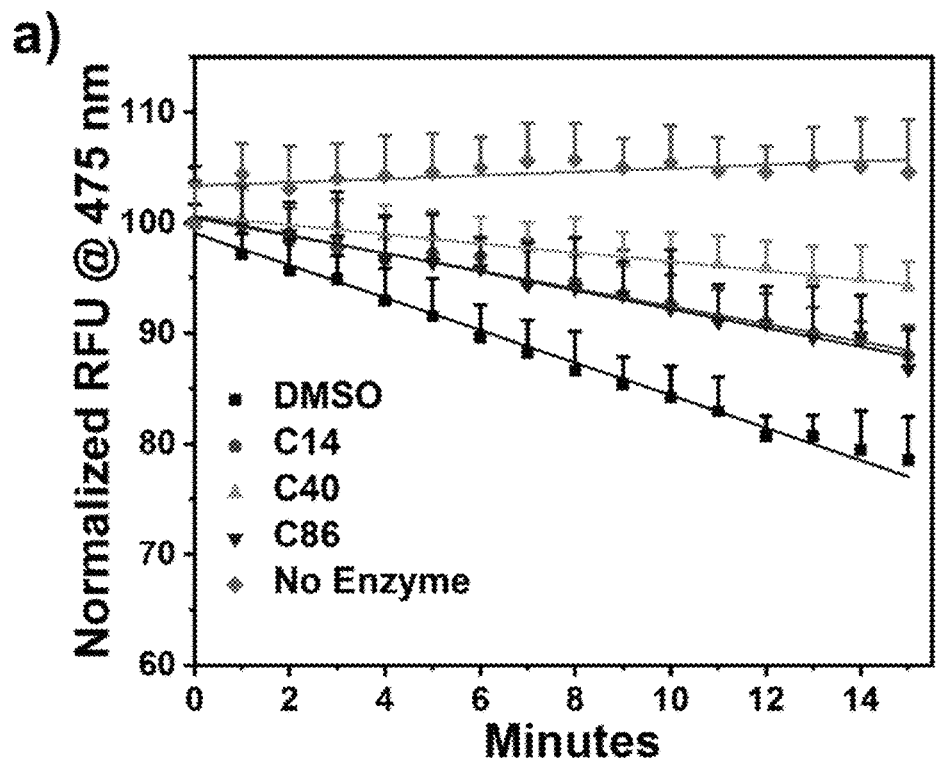
FIGS. 4A-4B: MTB CdnP c-di-AMP hydrolysis in the presence and absence of identified HTS hits visualized with the coralyne.
Figure 4B:
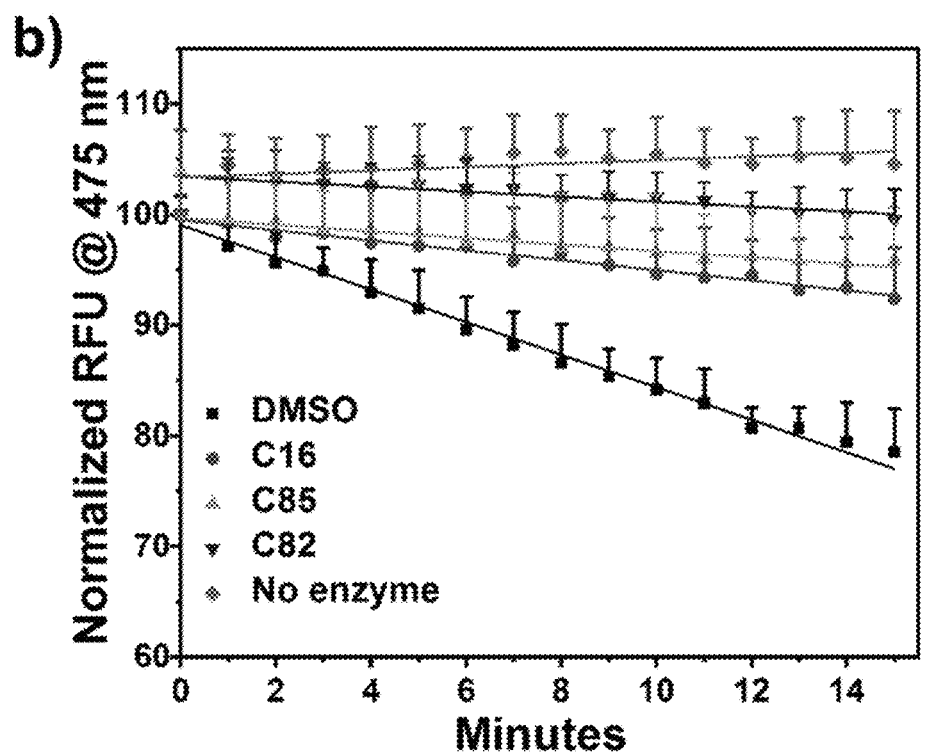

The coralyne assay, developed by our group,[17] was used to conduct high throughput screens for MTB CdnP inhibitors. The assay capitalizes on the fact that c-di-AMP protects coralyne from iodide quenching via the formation of an inclusion complex with c-di-AMP (FIG. 2). Following the formation of the c-di-AMP-coralyne complex, coralyne fluorescence emission is greatly enhanced. Since c-di-AMP enhance coralyne fluorescence emission in a concentration dependent manner while AMP does not coralyne assay can be used to track c-di-AMP degradation by MTB CdnP and therefore could be used to identify MTB CdnP inhibitors. Prior to conducting the HTS, the assay was optimized for both kinetics and endpoint analysis. Experimental parameters were adjusted to obtain an optimal screening window, and at the same time ensuring that MTB CdnP kinetics stayed in the linear range. The screening window was quantified using the Z-factor, a screening window coefficient. Z-factor is reflective of both the assay signal dynamic range and the data variation associated with the measurements (Eqn. 1)[18]. An ideal assay for HTS ought to have a Z-factor between 1 and 0.5. Hence, we optimized the experimental conditions to obtain ideal assay conditions for the HTS assay. The Z-factors for different c-di-AMP concentrations, chosen to be close to the apparent Km (obtained via the coralyne assay) were computed. The concentration of potassium iodide, KI, which is used as an anion quencher to reduce the fluorescence of the unbound coralyne[17], was also varied and Z-factor computed. Optimal assay conditions for both kinetic (Z-factor=0.61) and endpoint (Z-factor=0.71) approaches were found to be 70 $\mu M$ c-di-AMP and 10 mM KI. Thus the HTS was conducted with these conditions. 90,000 compounds (Purdue Chemical Genomics Facility compound library), which included kinase inhibitor library, natural products, and diversity library, were screened for CdnP inhibition. Compounds that exhibited over 40% inhibition were selected as potential MTB CdnP inhibitors (FIG. 3 and FIG. 4).

Figure 5A:
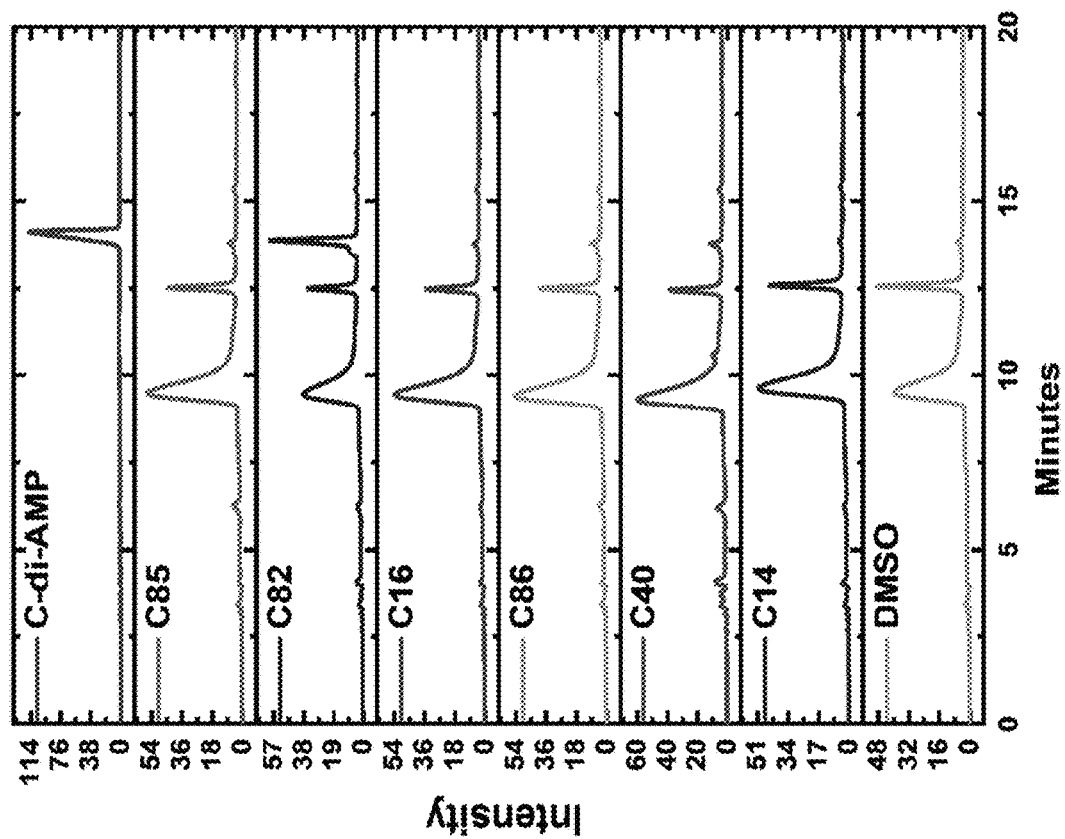
FIGS. 5A-5B: Inhibition of MTB CdnP enzymatic activity by compounds, analyzed via High Performance Liquid Chromatography (HPLC).
Figure 5B:
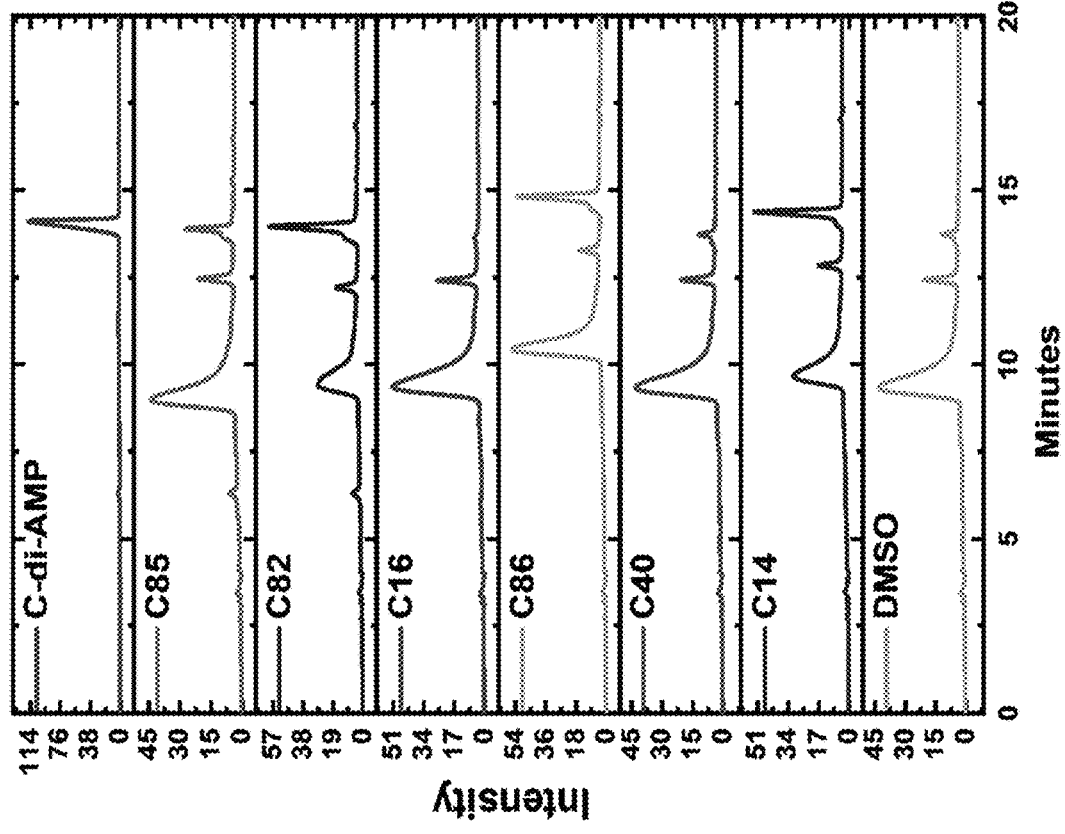

Next, we ran HPLC based enzymatic reactions to confirm the putative CdnP inhibitors identified from the HTS. MTB CdnP was incubated in the presence and the absence of the hit compounds, reactions were quenched and then analyzed via liquid chromatography. The reactions were analyzed at two different time points (after 3 h and 12 h incubations). All of the compounds, save C16 and C40, showed substantial inhibition after 3 h incubation; C86, C82, and C14 showed the most potent inhibitory effects (FIG. 5a). Only C82 retained any inhibitory effect after an overnight incubation (FIG. 5b) and thus we designated it as our most potent MTB CdnP inhibitor. The fact that C16, the only molecule lacking the N-phenyl-6-oxo-pyrimidine-1-carboxamide moiety did not show any activity after 3 h incubation indicates that this moiety is important for inhibitory activity. The lower enzymatic inhibition by C40, compared to C14 and C86, indicates that substituents of the phenyl ring impacts activity and hence provides a strategy to improve inhibitor potency in future optimization campaigns.

Figure 6:
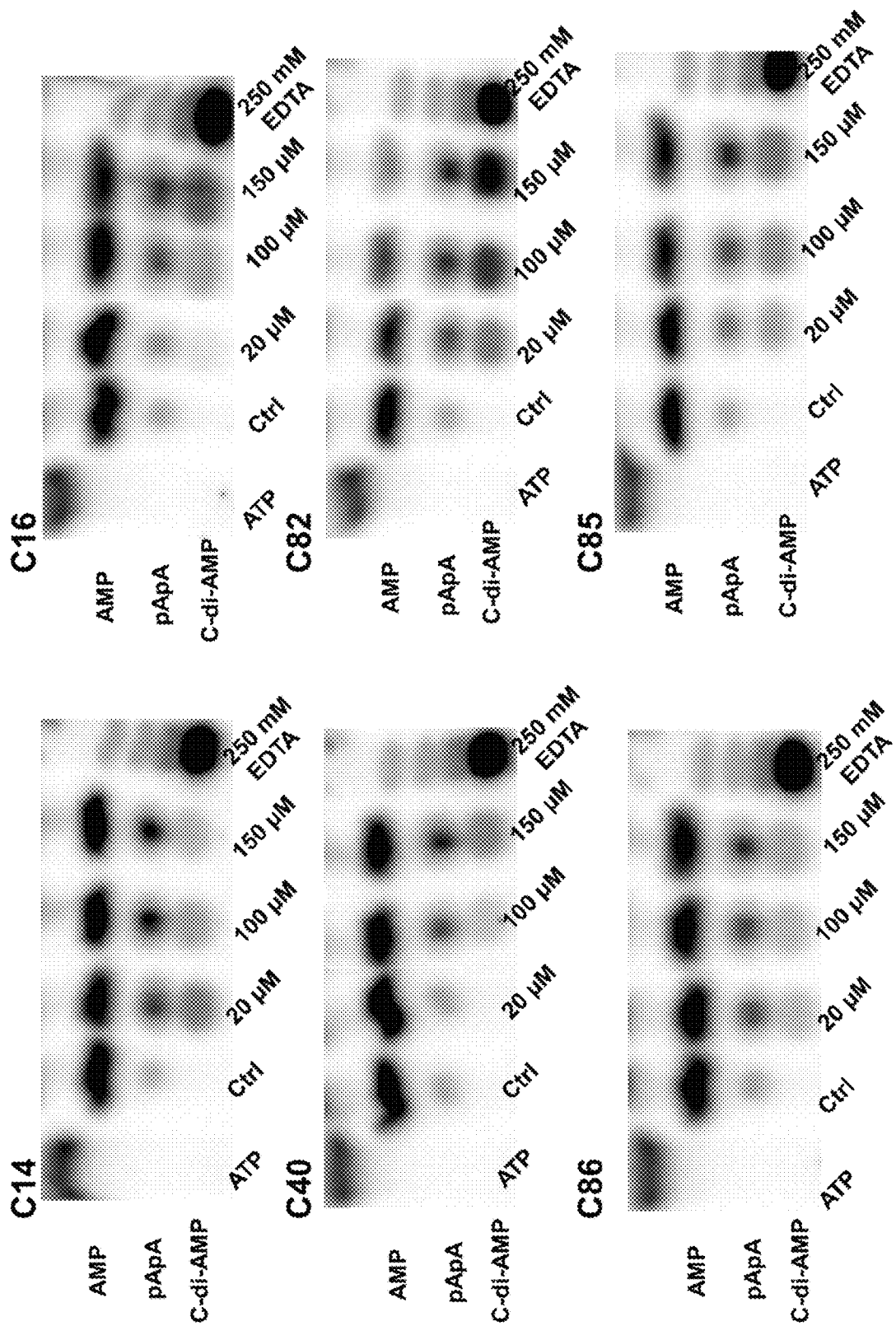
FIG. 6: Inhibition of MTB CdnP enzymatic activity by compounds, analyzed via thin-layer chromatography (TLC). Visualization of c-di-AMP cleavage by 0.5 µM MTB CdnP in the presence and absence of varying hit compounds concentration. 'Ctrl'=control group treated with dimethyl sulfoxide (DMSO). Experiment conducted with 0.5 µM CdnP, 70 µM C-di-AMP, 6.6 nM $^{32}$P—C-di-AMP in 1× reaction buffer (50 mM Tris-HCl pH 8.0, 5 mM $MnCl_2$) and incubated for 1 h at 37° C.

We further confirmed the inhibitory effects our hit compounds using comparative radioisotope thin layer chromatography (TLC). $^{32}$P-c-di-AMP was synthesized by incubating MTB DisA, a c-di-AMP synthase enzyme, with hot ATP ($^{32}$P-ATP) and cold ATP as previously reported[19]. MTB CdnP reactions were set up in the presence and absence of varying inhibitor concentrations (20 to 150 µM), and c-di-AMP hydrolysis visualized via TLC. Ethylenediaminetetraacetic acid (ETDA) was used as a surrogate for a potent inhibitor. MTB CdnP enzymatic activity requires $Mn^{2+}$ cofactor, hence divalent metal chelators such as ETDA can quench the reaction. Therefore, in the presence of ETDA we expected c-di-AMP cleavage to be diminished (FIG. 5). All compounds showed a concentration dependent inhibitory activity with C82 exhibiting the most potent inhibition (FIG. 6). C40 and C16 were the least potent compounds. C40 was the only compound that did not show any inhibitory effect at 20 µM concentration (FIG. 6). C16 exhibited very little inhibitory effect at 20 µM (FIG. 6). From the three complementary assays (coralyne, HPLC and TLC) we concluded that C82 was the most potent inhibitor. To confirm this, we also determined the $IC_{50}$ of enzyme inhibition by compounds using the safer and more convenient coralyne assay. Consistent with the earlier data C82 was the most potent compound. C82, C85, C14, C40, C16 and C86 inhibited MTB CdnP enzymatic activity (50 nM MTB CdnP and 80 µM c-di-AMP) with $IC_{50}$ values of 17.4 µM, 21.4 µM, 24.5 µM, 34.6 µM, 48.9 µM, and >60 µM respectively.

Figure 7A:
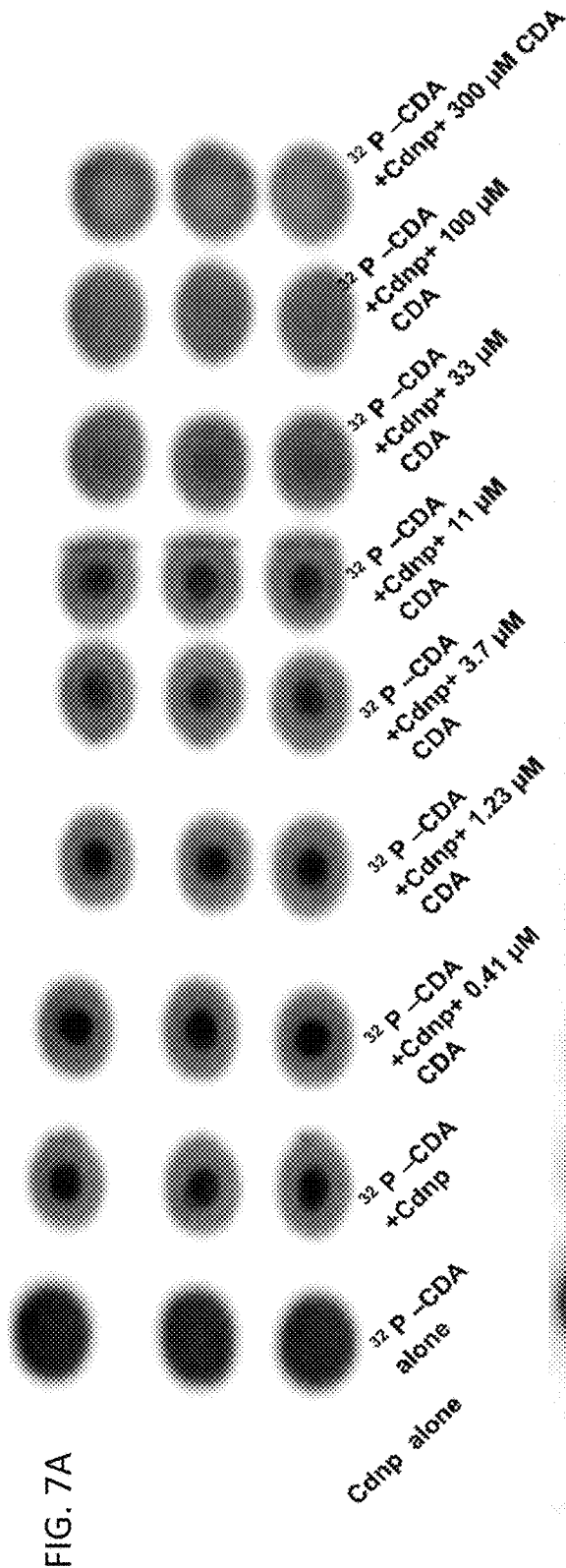
FIGS. 7A-7D: C82 does not displace c-di-AMP from MTB CdnP.
Figure 7B:
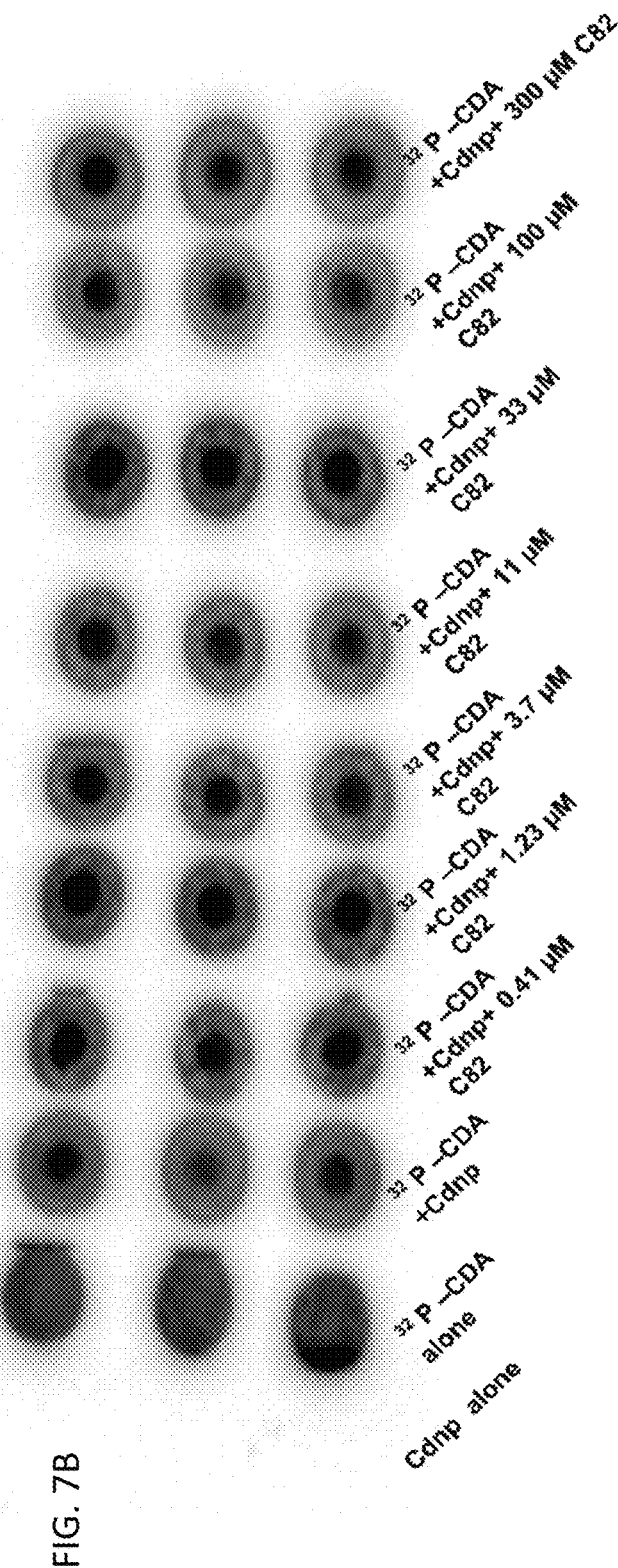
Figure 7C:
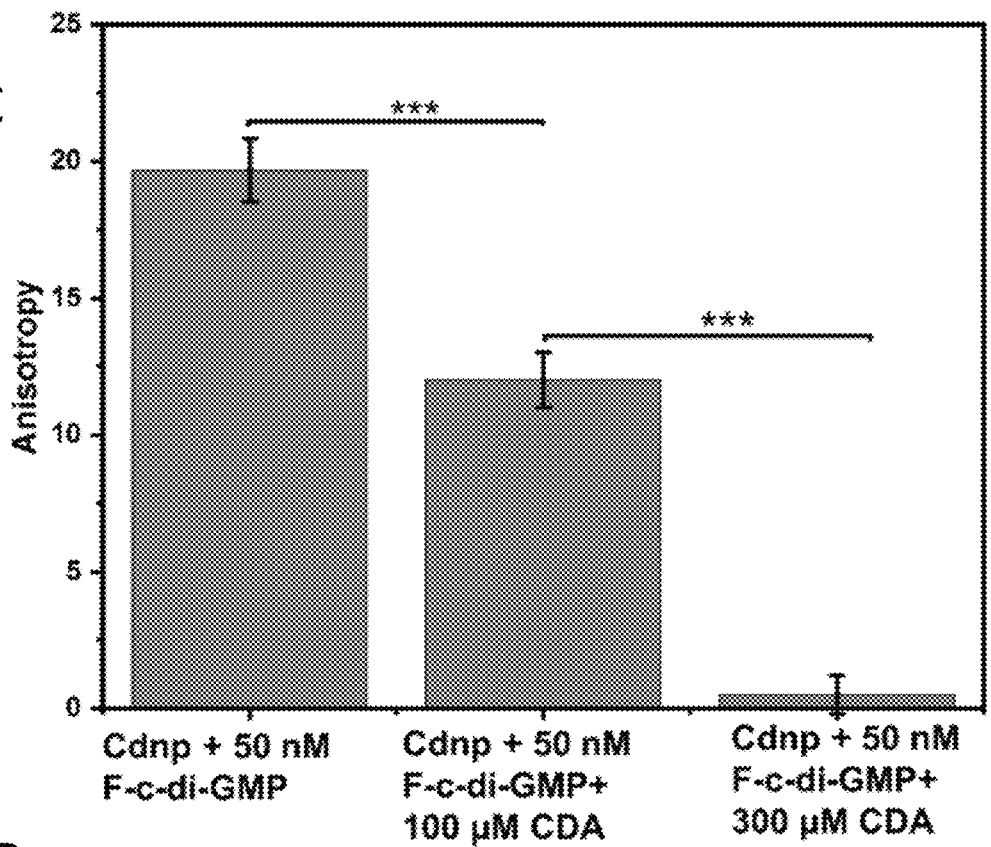
Figure 7D:
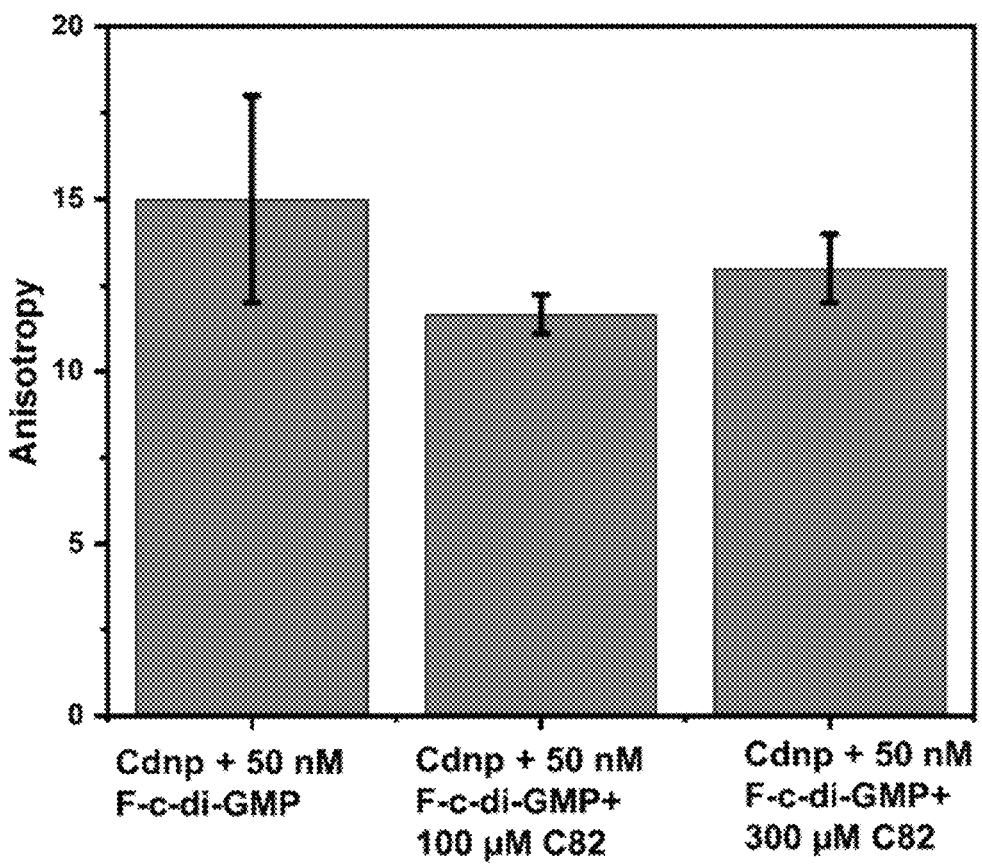
Figure 8:
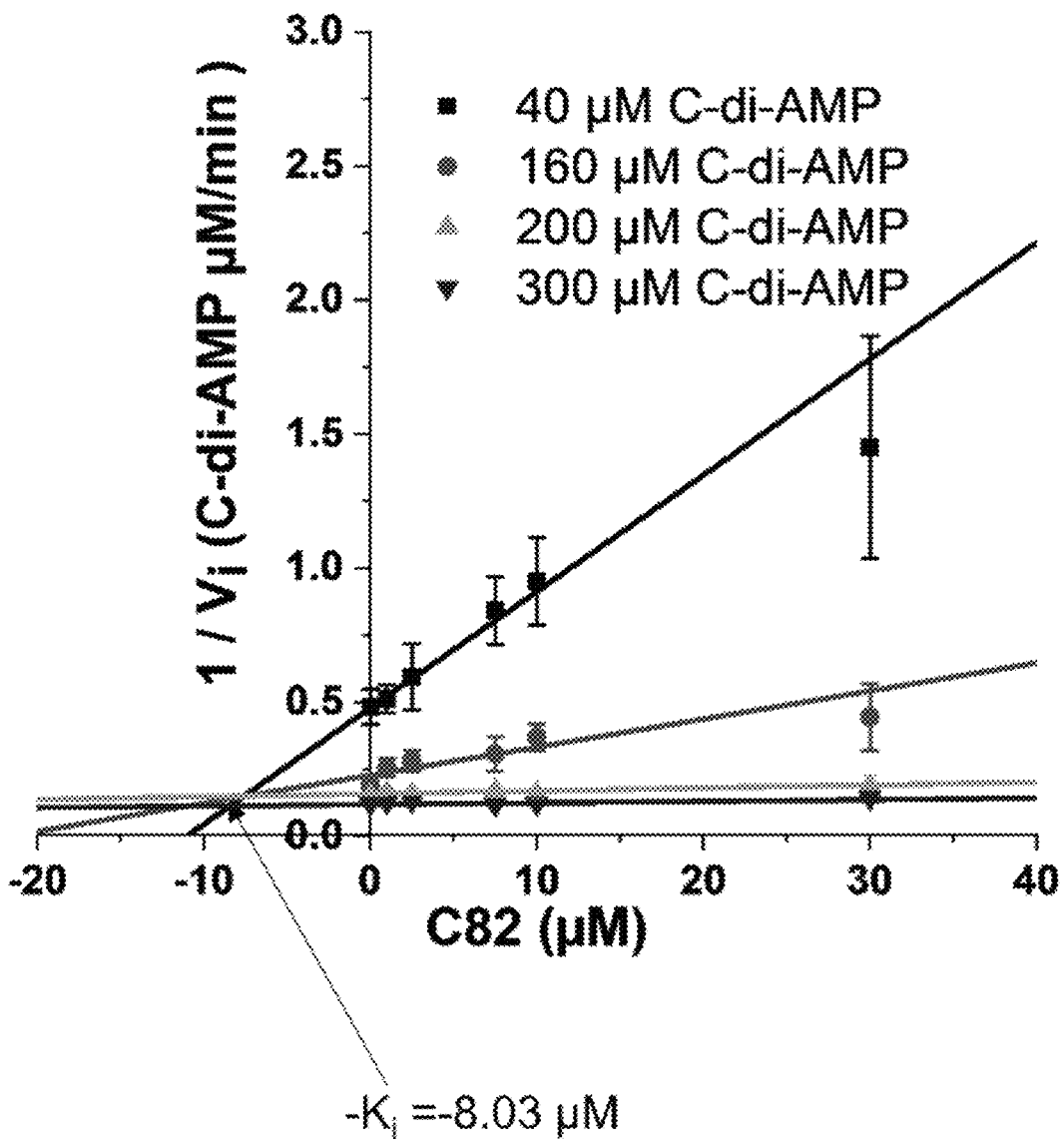
FIG. 8: C82 Dixon plot. Initial velocity was determined using slope of c-di-AMP hydrolysis kinetics. Experiment conducted at 30° C. with 50 nM MTB CdnP, 10 mM KI, 10 µM coralyne, in 1× reaction buffer (50 mM Tris-HCl pH 8.0, 5 mM $MnCl_2$) optimized to keep the hydrolysis in the linear range.

Next, we sought to determine C82 mode of inhibition. Firstly, we confirmed that C82 does indeed bind to MTB CdnP, using intrinsic fluorescence assay[20]. MTB CdnP intrinsic fluorescence decayed in C82 concentration dependent manner, confirming C82 does bind to MTB CdnP. We then determined whether C82 could displace bound c-di-AMP from MTB CdnP. To do this, we incubated MTB CdnP with radiolabeled c-di-AMP and tried to displace the bound c-di-AMP with different concentrations of C82 using the differential radial capillary action of ligand (DRaCALA) assay.[5b] Whiles, unlabeled c-di-AMP could displace radiolabeled c-di-AMP from MTB CdnP (FIG. 7a), C82 even at 300 µM, did not displace radiolabeled c-di-AMP from the enzyme (FIG. 7b). We also used a secondary fluorescent polarization displacement assay to confirm this finding. Briefly, fluorescent labeled c-di-GMP was incubated with MTB CdnP and treated with different concentrations of C82, or c-di-AMP in the presence of calcium to inhibit the cleavage of the bound CDN'". Consistent with the DRaCALA results, C82 did not displace the fluorescent labeled c-di-GMP from MTB CdnP, whiles the unlabeled c-di-AMP was able to displace fluorescent labeled c-di-GMP from MTB CdnP in a concentration dependent manner (FIG. 7c, 7d). We therefore concluded that C82 inhibits MTB CdnP by binding to a non-cyclic dinucleotide binding site. Kinetics studies reveal that C82 inhibits MTB CdnP with an apparent inhibition constant of approximately 8 µM (FIG. 8). Future structural work, beyond the scope of this work should help clarify the binding site of C82.

We proceeded to investigate if C82 was promiscuous CDN phosphodiesterase (PDE) inhibitor. We screened C82 against three bacterial CDN PDEs (Ybyt, RocR and GBS-CdnP), one mammalian CDN PDE, ENPP1 and poxin, a viral CDN PDE. Ybyt is a *Bacillus subtilis* CDN PDE that hydrolyzes both c-di-AMP and c-di-GMP[21]. RocR is a *P. aeruginosa* c-di-GMP PDE and GBS-CdnP is Group B *Streptococcus* (GBS) c-di-AMP PDE[22]. GBS-CdnP, just like MTB CdnP, has been shown to dampen STING-dependent type I interferon induction[22b]. Mammalian ENPP1, is capable of degrading both cGAMP and bacterial CDNs[10a]. Consequently, ENPP1 is an excellent target for development of immunotherapy agents for both cancer and infections management. Poxins (poxvirus immune nuclease) are 2' 3'-cGAMP-degrading enzymes, whose activities result in dampened STING-dependent signaling[11]. For selectivity studies, the assays conditions were optimized to ensure most of the substrate was not hydrolyzed. C82 did not inhibit any of these enzymes; thus C82 can be considered as MTB CdnP specific inhibitor (at least when compared to five other cyclic dinucleotide PDEs). Lastly, we evaluated C82 cytotoxicity against mammalian cells. Up to 100 µM, C82 did not significantly inhibit cell viability.

Conclusion: Due to the vital roles of CDNs in bacteria cell physiology and the modulation of the innate immune system, CDNs metabolizing enzymes are attractive therapeutic targets. Several inhibitors of bacterial CDN synthase enzymes have been reported. In contrast, only one non-nucleotide bacterial CDNs PDE inhibitor has been described. To fill in the gap, we embarked on the search of a MTB CdnP PDE inhibitor, which could be used as a tool compound or potential therapeutic. To our knowledge, this is the first report of non-nucleotide MTB CdnP PDE selective inhibitor. C82 and analogs thereof, which contain the 2-(4-oxothieno [2,3-d]pyrimidin-3(4H)-yl)acetamide or 2-(4-oxoquinazolin-3(4H)-yl)acetamide moieties, are excellent starting compounds to develop novel cyclic dinucleotide phosphodiesterase inhibitors.

Cyclic mononucleotide phosphodiesterase inhibition (PDE5A): 10 µM of compound was added to PDE5A in Buffer (10 mM Tris, pH 7.5, 5 mM MgCl2, 0.01% Brij 35, 1 mM DTT, and 1% DMSO). 1 µM cGMP was added and the reaction was incubated for 1 h. The assay used detects the reaction product, GMP, by Transcreener Fluorescence polarization assay (Reaction Biology).

| Compound | % inhibition (PDE5A) |
|---|---|
| C86 | 67 |
| C16 | 92.00 |
| C14 | 86.00 |
| C82 | 32.00 |
| C25 | 91.00 |
| C40 | 85.00 |
| Methoxyquinazoline [Control IC50 (M)] | 5.58E−06 |

Material and Methods:
Protein Expression and Purification

Overnight cultures of *E. coli* BL21(DE3) containing plasmid of interest were inoculated in 1 L terrific broth media supplemented with selection antibiotics and cultured to exponential phase (OD=0.6) at 37° C. MTB CdnP plasmid was a gift from William R Bishai[10a]. Ybyt plasmid was a gift from Zhao-xun Liang[23]. GBS plasmid was a gift from Pierre-Alexandre Kaminski[22b]. Poxin plasmid was a gift from Philip J. Kranzusch[11]. RocR plasmid was a gift from Zhao-Xun Liang[24]. Cells was then supplemented with 0.5 mM IPTG to induce expression. After addition of IPTG, cells were incubated at 16° C. for 18 h. The cells were then centrifuged at 4° C. for 25 min and the pellet resuspended in lysis buffer (25 mM Tris-HCl, 500 mM NaCl and 20 mM imidazole pH=8.2 for MTB CdnP, DisA and YybT, 20 mM Hepes-KOH, pH=7.5, 400 mM NaCl, 30 mM imidazole, 10% glycerol and 1 mM DTT for poxin) supplemented with 1 mM PMSF. The cells were lysed by sonication and centrifuged at 22,000 rpm for 25 min. The supernatants were passed through HisTrap HP 5 mL columns (GE). Wash buffer (25 mM Tris-HCl, pH=8.2, 500 mM, NaCl and 50 mM imidazole for MTB CdnP, GBS CdnP and YybT, 20 mM Hepes-KOH, pH=7.5, 1M NaCl, 30 mM imidazole, 10% glycerol and 1 mM DTT for poxin) was then passed through the column. The wash step was repeated once. Proteins were eluted with 25 mM Tris-HCl, pH=8.2, 500 mM NaCl and 200 mM imidazole for MTB CdnP, DisA and YybT, 20 mM Hepes-KOH, pH=7.5, 400 mM NaCl, 300 mM imidazole, 10% glycerol and 1 mM DTT for poxin. Eluted proteins were then dialyzed and concentration determined by measuring absorbance at 280 nm.

C-di-AMP Synthesis

C-di-AMP used in this study was enzymatically synthesized using DisA. 20 mL reaction volume containing 1 mM ATP, and 2 µM DisA was set up. The reaction was incubated at 37° C. overnight. The reaction was stopped by denaturing at 95° C. for 5 min. The reaction was then filtered using a 3 K centrifugal filter (VWR International) and c-di-AMP purified using HPLC [COSMOSIL C18-MS-II Packed column (running buffers=0.1 M TEAA in water and acetonitrile)]. Gradient is as follows: 0-16 min: 99%-87% 0.1 M TEAA, 1%-13% acetonitrile, 16-23 min: 87%-10% 0.1 M TEAA, 13%-90% acetonitrile, 23-25 min: 10%-99% 0.1 M TEAA, 90%-1% acetonitrile. The purified c-di-AMP was dried with a speed vacuum and the residue was then re-suspended in water. C-di-AMP concentration was quantified by measuring absorbance at 260 nm.

IC$_{50}$ Determination

Reactions of 20 µL in volume containing 50 nM MTB CdnP, 100 µM c-di-AMP, 10 mM KI, 10 µM coralyne in 1× reaction buffer (50 mM Tris-HCl pH 8.0, 5 mM MnCl$_2$) supplemented with 0.0025% Triton X-100 and varying concentrations of identified hits were set up in Greiner FLUOTRAC 384 well plate. Experimental parameters optimized to keep hydrolysis in the linear range. Real time c-di-AMP hydrolysis kinetics was monitored by measuring fluorescence intensity at $\lambda_{em}$=475 nm ($\lambda_{ex}$=420 nm) at 2 min intervals for 10 min. Reader (Biotek Cytation 5 multi-mode reader) chamber temperature set to 30° C. Slope of the curve used to estimate initial velocity. Experiment done in triplicates.

Calibration Curves Generation

10 µM coralyne in 1×MTB CdnP reaction buffer (50 mM Tris-HCl, pH=9.0, 5 mM MnCl$_2$) was mixed with varying concentrations of c-di-AMP or AMP and fluorescence emission at 475 nm following excitation at 420 nm measured.

Coralyne Based Monitoring of MTB CdnP Reaction

Reactions of 100 µl in volume containing 50 nM MTB CdnP, 10 µM coralyne, 3 mM KI, and varying concentrations of c-di-AMP in 1× reaction buffer (50 mM Tris-HCl, pH=9.0, 5 mM MnCl$_2$ and various C82 concentrations were set up in Greiner FLUOTRAC 96 well plate. Real time c-di-AMP hydrolysis was monitored by measuring fluorescence intensity at $\lambda_{em}$=475 nm ($\lambda_{ex}$=420 nm) at 1 min intervals for 10 min (reaction still in linear range). Reader (Biotek Cytation 5 multi-mode reader) chamber temperature set to 30° C. Slope of the curve used to estimate initial velocity. Experiment done in triplicates. c-di-AMP calibration curve was used to estimate change in c-di-AMP concentration at the end of reaction.

High-Throughput Screening

MTB CndP reaction parameters were optimized to yield a Z-factor in 0.5-1 range. 0.5 µM MTB CdnP and 10 µM coralyne were used. Z-factor was computed with the following equation:

$$a.\ Z = 1 - \frac{3(\sigma_p + \sigma_n)}{|\mu_p - \mu_n|} \quad \text{Equation 1}$$

Where $\sigma_p$ and $\sigma_n$ are the standard deviation of the positive control and negative control respectively, $\mu_p$ is the mean of the positive control and $\mu_n$ is the mean of the negative control.

HTS was conducted at the chemical genomics facility at the Purdue Institute for Drug Discovery. Reactions of 20 µL in volume containing 70 µM c-di-AMP, 10 µM coralyne, 10 mM KI, 5 mM MnCl$_2$, 10 µM compound from the library and 0.5 µM MTB CdnP in reaction buffer (50 mM Tris-HCl, pH=9.0) were set up in the following order. 10 µl of a reaction mix (1× reaction buffer, 2× c-di-AMP, 2× coralyne, 2× MnCl$_2$, and 2× KI) was dispensed into Greiner FLUOTRAC 384 plates. Compounds were then dispensed with a robot, and finally 10 µl of enzyme mix (2×MTB CdnP in 1× reaction buffer) was added to the plates. Fluorescence readings were taken immediately following the addition of the enzyme for kinetic-based screens. C-di-AMP hydrolysis was monitored by measuring fluorescence intensity at $\lambda_{em}$=475 nm ($\lambda_{ex}$=420 nm) at 1 min intervals for 15 min. On the other hand, plates were incubated for 30 min at 37° C. The reactions were then stopped by addition of 30 mM EDTA and endpoint fluorescence measured.

HPLC Analysis

MTB CdnP reactions (70 µM C-di-AMP, 100 nM MTB CdnP, 1× reaction buffer) were set up in the presence and absence of 20 µM compound, incubated at 37° C. for 3 h or 12 h. Reactions were quenched by heating at 95° C. for 5 min. The reaction was then filtered using a 3 K centrifugal filter (VWR International) and analyzed using HPLC as described above.

For GBS CdnP, reactions containing 50 µM c-di-AMP, 1× reaction buffer (50 mM Tris-HCl, pH=7.5, and 5 mM MnCl$_2$) and 100 nM GBS CdnP were set up in the presence and absence of C82. Reactions were incubated at room temperature for 15 min. Reactions were quenched by heating at 95° C. for 5 min. The reaction was then filtered using a 3 K centrifugal filter (VWR Int'l) and analyzed using HPLC as described.

For poxin, reactions containing 20 µM 2'3 cGAMP (Chemietek), 1× reaction buffer (20 mM Hepes-KOH, pH=7.5) and 5 nM poxin were set up in the presence and absence of C82. Reactions were incubated at room temperature for 20 min. Reactions were quenched by heating at 95° C. for 5 min. The reaction was then filtered using a 3 K centrifugal filter (VWR International) and analyzed using HPLC as described above.

For Yybt, reactions containing 70 µM c-di-AMP, 1× reaction buffer (0.1M Tri-HCl, pH=8.0, 20 mM KCl, and 0.5 mM MnCl$_2$) and 1 µM Yybt were set up in the presence and absence of C82. Reactions were incubated at 37° C. for 60 min. Reactions were quenched by heating at 95° C. for 5 min. The reaction was then filtered using a 3 K centrifugal filter (VWR International) and analyzed using HPLC as described above.

For RocR, reactions containing 25 µM C-di-GMP, 1× reaction buffer (100 mM Tris-HCl, pH=8.0, 20 mM KCl and 25 mM MgCl$_2$) and 10 nM RocR were set up in the presence and absence of C82. Reactions were incubated at 37° C. for 60 min. Reactions were quenched by heating at 95° C. for 5 min. The reaction was then filtered using a 3 K centrifugal filter (VWR International) and analyzed using HPLC as described above.

For ENNP1, reactions containing 25 µM cGAMP, 1× reaction buffer (50 mM Tris, pH 9.5 250 mM NaCl) and 4.58 nM ENNP1 were set up in the presence and absence of C82. Reactions were incubated at 37° C. for 60 min. Reactions were quenched by heating at 95° C. for 5 min. The reaction was then filtered using a 3 K centrifugal filter (VWR International) and analyzed using HPLC as described above.

Radiolabeling Experiments $^{32}$P-c-di-AMP was synthesized by incubating 0.033 µM [α$^{32}$P]-ATP (Perkin Elmer), 3 mM ATP and 10 µM DisA in a buffer containing 40 mM Tris-HCl, pH 7.5, 100 mM NaCl and 10 mM MgCl$_2$ at 37° C. overnight. The DisA reaction was stopped by heat denaturing. For the inhibition test, 0.5 µM MTB CdnP was incubated with 25 µM c-di-AMP, 3.3 nM $^{32}$P-c-di-AMP, and varying concentrations of compounds in MTB CdnP reaction buffer for 1 h at 37° C. 1 µL of reaction mixture was applied on a cellulose TLC plate (EMD Millipore) and left to dry at room temperature.

The TLC plates were developed in saturated (NH$_4$)$_2$SO$_4$: 1.5 M KH$_2$PO$_4$ buffer. The plates were then dried by heating on a hot plate at 95° C. followed by an overnight exposure on GE Storage Phosphor screen. The screen was visualized with Typhoon™ FLA 9500 biomolecular imager.

Intrinsic Fluorescence

Solutions containing 2 µM MTB CndP, and varying concentrations of C82 in 1× PBS were incubated for 30 min at room temperature. Fluorescence spectra were obtained by measuring fluorescence intensities in the 310 nm to 400 nm range following an excitation at 290 nm wavelength.

Differential Radial Capillary Action of Ligand Assay (DRaCALA)

Reaction mixtures containing 20 µM MTB CdnP, 1× reaction buffer (50 mM Tris-HCl, pH=7.5), 5 mM calcium chloride, 200 pM $^{32}$P c-di-AMP, and varying concentrations of c-di-AMP or C82 (total volume=20 µL) were set up and incubated at room temperature for 10 min. 5 µl of the reaction mixture was pipetted onto dry untreated nitrocellulose membrane (GE Healthcare) and allowed to dry at room temperature. The nitrocellulose membrane was exposed to the GE Storage Phosphor screen for 8 h and then visualized with Typhoon™ FLA 9500 biomolecular imager.

Fluorescence Polarization Competition Assay

Reaction mixtures containing 150 µM MTB CdnP, 1× reaction buffer (50 mM Tris-HCl, pH=7.5), 5 mM calcium chloride, 50 nM fluorescein labeled c-di-GMP (2'-Fluo-AHC-c-diGMP, Biolog) and varying concentrations of c-di-AMP or C82 (total volume=20 µL) were set up and incubated at room temperature for 10 min. Fluorescence polarization was determined using Biotek Cytation 5 multi-mode reader (excitation 485 nm/20 and emission 528 nm/20). Anisotropy was calculated using the GEN 5™ microplate reader and imaging software.

Cell Viability

200 µL of culture medium containing 4000 cells was pipetted into each well of 96 well plate and incubated at 37° C. with 5% CO$_2$ for 18 h. The cells were then supplemented with compounds or dimethyl sulfoxide for the control group. The cells were incubated for an additional 24 h and cell viability determined with the CellTiter-Blue® Cell Viability Assay. Briefly, 10 µL of the CellTiter-Blue reagent was added to the wells, incubated for 4 h at 37° C. with 5% CO$_2$ and cell viability determined by measuring fluorescence (excitation 560 nm and emission 590 nm) with Biotek Cytation 5 multi-mode reader. Culture medium=Dulbecco's Modified Eagle Medium+10% Fetal Bovine Serum. Cell lines=MDA-MB-231, and MRC-5.

General Procedure for the Synthesis of Analogs:

A round bottom flask was charged with corresponding acid (1.2 eq) and diisopropylethylamine (4 eq) in DMF (5 mL) was stirred at room temperature for 30 minutes. Then, amine (1 eq) was added and the reaction was continued for 12 hours at room temperature. Next, the reaction mixture was concentrated, diluted with ethyl acetate (20 mL), washed twice with water (10 mL), once with brine (10 mL), dried over sodium sulfate, filtered, and concentrated under reduced pressure. The crude reaction mixture was purified via flash column chromatography (hexanes:ethyl acetate 60:40) to give desired product.

Compound Characterization:

2-(6-ethyl-4-oxothieno[2,3-d]pyrimidin-3(4H)-yl)-N-(3-methoxyphenyl)acetamide (HSDP-15)

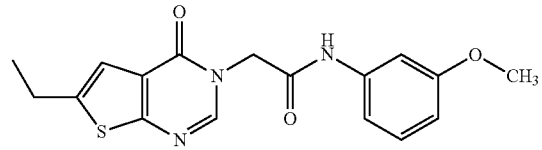

$^1$H NMR (500 MHz, DMSO-d$_6$) δ 10.4 (s, 1H), 8.3 (s, 1H), 7.3 (d, J=2.3 Hz, 1H), 7.2 (t, J=8.2 Hz, 1H), 7.1 (s, 1H), 7.1 (dd, J=8.1, 1.9 Hz, 1H), 6.6 (dd, J=8.2, 2.5 Hz, 1H), 4.8 (s, 2H), 3.7 (s, 3H), 2.9-2.8 (m, 2H), 1.3 (t, J=7.5 Hz, 3H).

2-(6-ethyl-4-oxothieno[2,3-d]pyrimidin-3(4H)-yl)-N-(4-methoxyphenyl)acetamide (HSDP-16)

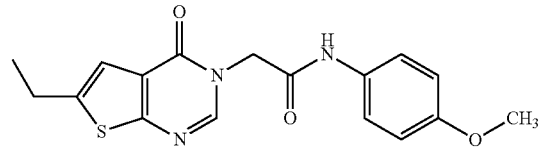 [SMILES: CCc1cc2c(=O)n(CC(=O)Nc3ccc(OC)cc3)cnc2s1]

$^1$H NMR (500 MHz, DMSO-d$_6$) δ 10.3 (s, 1H), 8.3 (s, 1H), 7.5 (d, J=9.1 Hz, 1H), 7.1 (s, 1H), 6.9 (d, J=9.1 Hz, 1H), 4.8 (s, 2H), 3.7 (s, 3H), 2.9 (qd, J=7.5, 1.2 Hz, 2H), 1.3 (t, J=7.5 Hz, 3H).

2-(6-ethyl-4-oxothieno[2,3-d]pyrimidin-3(4H)-yl)-N-(4-methoxypyridin-3-yl)acetamide (HSDP-17)

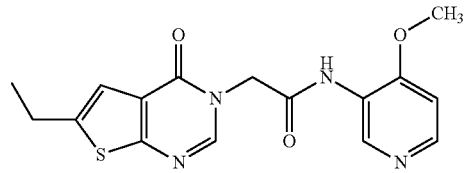 [SMILES: CCc1cc2c(=O)n(CC(=O)Nc3cnccc3OC)cnc2s1]

$^1$H NMR (500 MHz, DMSO-d$_6$) δ 10.5 (s, 1H), 8.8 (s, 1H), 8.3 (s, 1H), 8.2 (d, J=8.9 Hz, 1H), 7.1 (s, 1H), 6.9 (d,

J=8.9 Hz, 1H), 4.8 (s, 2H), 3.8 (s, 3H), 2.9 (qd, J=7.5, 1.2 Hz, 2H), 1.3 (t, J=7.5 Hz, 3H).

2-(6-ethyl-4-oxothieno[2,3-d]pyrimidin-3(4H)-yl)-N-(6-methoxypyridin-3-yl)acetamide (HSDP-18)

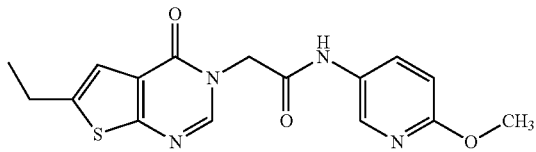 [SMILES: CCc1cc2c(=O)n(CC(=O)Nc3ccc(OC)nc3)cnc2s1]

¹H NMR (500 MHz, DMSO-d₆) δ 10.5 (s, 1H), 8.3 (d, J=3.2 Hz, 2H), 7.9 (dd, J=8.9, 2.7 Hz, 1H), 7.1 (s, 1H), 6.8 (d, J=8.9 Hz, 1H), 4.8 (s, 2H), 3.8 (s, 3H), 2.9 (qd, J=7.5, 1.2 Hz, 2H), 1.3 (J=7.5 Hz, 3H).

2-(6-ethyl-4-oxothieno[2,3-d]pyrimidin-3(4H)-yl)-N-(2-(trifluoromethoxy)phenyl)acetamide (HSDP-20)

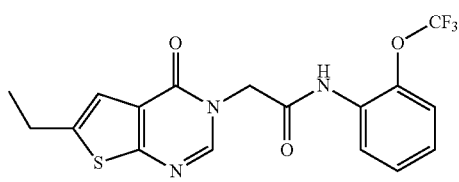 [SMILES: CCc1cc2c(=O)n(CC(=O)Nc3ccccc3OC(F)(F)F)cnc2s1]

¹H NMR (500 MHz, DMSO-d₆) δ 10.1 (s, 1H), 8.3 (s, 1H), 8.0 (d, J=8.9 Hz, 1H), 7.2 (dd, J=8.9, 2.7 Hz, 1H), 7.1 (s, 1H), 7.0 (dd, J=8.9, 2.7 Hz, 1H), 6.9 (d, J=8.9 Hz, 1H), 4.8 (s, 2H), 2.9 (qd, J=7.5, 1.2 Hz, 2H), 1.3 (t, J=7.5 Hz, 3H).

2-(6-ethyl-4-oxothieno[2,3-d]pyrimidin-3(4H)-yl)-N-phenylacetamide (HSDP-23)

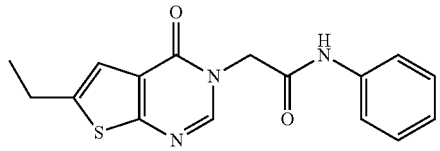 [SMILES: CCc1cc2c(=O)n(CC(=O)Nc3ccccc3)cnc2s1]

¹H NMR (500 MHz, DMSO-d₆) δ 10.4 (s, 1H), 7.6-7.5 (m, 2H), 7.3 (t, J=7.9 Hz, 2H), 7.1 (s, 1H), 7.1 (t, J=7.6 Hz, 1H), 4.8 (s, 2H), 2.9 (qd, J=7.5, 1.2 Hz, 2H), 1.3 (t, J=7.5 Hz, 3H).

N-cyclohexyl-2-(6-ethyl-4-oxothieno[2,3-d]pyrimidin-3(4H)-yl)acetamide (HSDP-24)

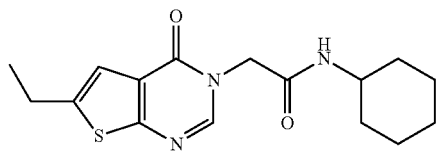 [SMILES: CCc1cc2c(=O)n(CC(=O)NC3CCCCC3)cnc2s1]

¹H NMR (500 MHz, DMSO-d₆) δ 8.2 (s, 1H), 8.2 (d, J=7.7 Hz, 1H), 7.1 (s, 1H), 4.6 (s, 2H), 3.6-3.5 (m, 2H), 2.8 (qd, J=7.5, 1.2 Hz, 2H), 1.8-1.6 (m, 4H), 1.5 (dd, J=10.7, 6.6 Hz, 1H), 1.3-1.1 (m, 8H).

N-(adamantan-1-yl)-2-(6-ethyl-4-oxothieno[2,3-d]pyrimidin-3(4H)-yl)acetamide (HSDP-25)

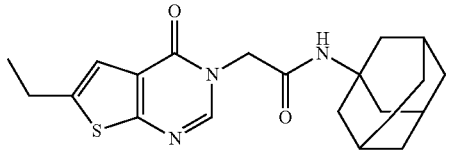 [SMILES: CCc1cc2c(=O)n(CC(=O)NC34CC5CCC(CC(C5)C3)C4)cnc2s1]

¹H NMR (500 MHz, DMSO-d₆) δ 8.2 (s, 1H), 8.2 (d, J=7.4 Hz, 1H), 7.1 (s, 1H), 4.7 (s, 2H), 3.8 (d, J=7.4 Hz, 1H), 2.8 (q, J=7.5 Hz, 2H), 2.0 (d, J=12.8 Hz, 2H), 1.8-1.6 (m, 11H), 1.5 (d, J=12.7 Hz, 2H), 1.2 (t, J=7.5 Hz, 3H).

N-(bicyclo[1.1.1]pentan-2-yl)-2-(6-ethyl-4-oxothieno[2,3-d]pyrimidin-3(4H)-yl)acetamide (HSDP-26)

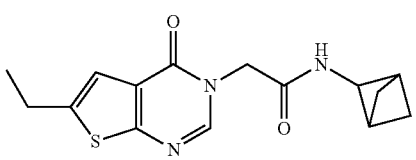 [SMILES: CCc1cc2c(=O)n(CC(=O)NC3C4CC3C4)cnc2s1]

¹H NMR (500 MHz, DMSO-d₆) δ 8.2 (s, 1H), 8.2 (d, J=7.5 Hz, 1H), 7.1 (s, 1H), 4.7 (s, 2H), 3.8 (t, J=7.5 Hz, 1H), 2.8 (qd, J=7.5 Hz, 2H), 2.6 (m, 2H), 2.0-1.7 (m, 2H), 1.6-1.4 (m, 2H), 1.2 (t, J=7.5 Hz, 3H).

2-(6-ethyl-4-oxothieno[2,3-d]pyrimidin-3(4H)-yl)-N-(2-(trifluoromethyl)phenyl)acetamide (HSDP-27)

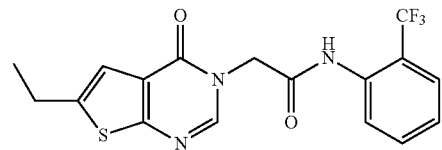 [SMILES: CCc1cc2c(=O)n(CC(=O)Nc3ccccc3C(F)(F)F)cnc2s1]

¹H NMR (500 MHz, DMSO-d₆) δ 10.0 (s, 1H), 8.3 (s, 1H), 7.7 (m, 2H), 7.5 (d, J=8.2 Hz, 1H), 7.3 (dd, J=8.2, 2.1 Hz, 1H), 7.1 (s, 1H), 4.8 (s, 2H), 2.9 (qd, J=7.5, 1.2 Hz, 2H), 1.3 (t, J=7.5 Hz, 3H).

N-(4-chloro-3-fluorophenyl)-2-(6-ethyl-4-oxothieno[2,3-d]pyrimidin-3(4H)-yl)acetamide (HSDP-28)

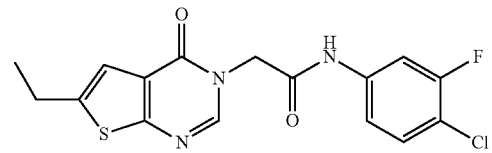 [SMILES: CCc1cc2c(=O)n(CC(=O)Nc3ccc(Cl)c(F)c3)cnc2s1]

¹H NMR (500 MHz, DMSO-d₆) δ 10.4 (s, 1H), 8.3 (s, 1H), 7.7 (s, 1H), 7.5 (d, J=8.5 Hz, 1H), 7.4 (d, J=8.5 Hz, 1H), 7.1 (s, 1H), 4.8 (s, 2H), 2.9 (qd, J=7.5, 1.2 Hz, 2H), 1.3 (t, J=7.5 Hz, 3H).

2-(6-ethyl-4-oxothieno[2,3-d]pyrimidin-3(4H)-yl)-N-(3-(methylthio)phenyl)acetamide (HSDP-29)

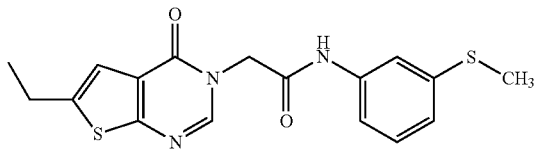

¹H NMR (500 MHz, DMSO-d₆) δ 10.3 (s, 1H), 8.3 (s, 1H), 7.7 (d, J=2.3 Hz, 1H), 7.5 (d, J=8.2 Hz, 1H), 7.4 (dd, J=8.1, 1.9 Hz, 1H), 7.3 (d, J=8.1 1H), 7.1 (s, 1H), 4.8 (s, 2H), 2.9-2.8 (m, 2H), 2.4 (s, 3H), 1.3 (t, J=7.5 Hz, 3H).

N-(benzo[d][1,3]dioxol-5-yl)-2-(6-ethyl-4-oxothieno[2,3-d]pyrimidin-3(4H)-yl)acetamide (HSDP-30)

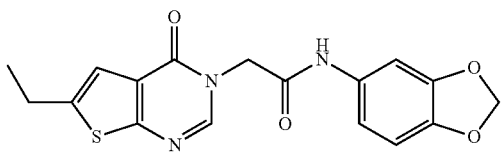 [SMILES: CCc1cc2c(=O)n(CC(=O)Nc3ccc4c(c3)OCO4)cnc2s1]

¹H NMR (500 MHz, DMSO-d₆) δ 10.4 (s, 1H), 8.3 (s, 1H), 7.3 (s, 1H), 7.1 (s, 1H), 7.0 (d, J=8.4 Hz), 6.8 (d, J=8.4 Hz, 1H), 5.9 (s, 2H), 4.8 (s, 2H), 2.9-2.8 (m, 2H), 2.4 (s, 3H), 1.3 (t, J=7.5 Hz, 3H).

N-(3-chloro-4-fluorophenyl)-2-(6-ethyl-4-oxothieno[2,3-d]pyrimidin-3(4H)-yl)acetamide (HSDP-31)

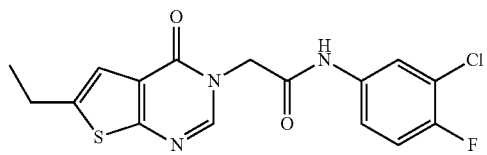 [SMILES: CCc1cc2c(=O)n(CC(=O)Nc3ccc(F)c(Cl)c3)cnc2s1]

¹H NMR (500 MHz, DMSO-d₆) δ 10.2 (s, 1H), 8.3 (s, 1H), 7.9 (s, 1H), 7.4 (d, J=8.2 Hz, 1H), 7.4 (d, J=8.2 Hz, 1H), 7.1 (s, 1H), 4.8 (s, 2H), 2.9 (qd, J=7.5, 1.2 Hz, 2H), 1.3 (t, J=7.5 Hz, 3H).

N-(5-chloro-2-methoxyphenyl)-2-(6-ethyl-4-oxothieno[2,3-d]pyrimidin-3(4H)-yl)acetamide (HSGN-0401)

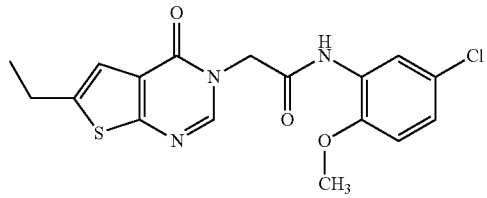 [SMILES: CCc1cc2c(=O)n(CC(=O)Nc3cc(Cl)ccc3OC)cnc2s1]

¹H NMR (500 MHz, DMSO-d₆) δ 10.4 (s, 1H), 8.3 (s, 1H), 7.9 (s, 1H), 7.2 (d, J=8.2 Hz, 1H), 7.1 (s, 1H), 6.9 (d, J=8.1 Hz, 1H), 4.8 (s, 2H), 3.8 (s, 3H), 2.9-2.8 (m, 2H), 1.3 (t, J=7.5 Hz, 3H).

N-(3-chloro-2-methoxyphenyl)-2-(6-ethyl-4-oxothieno[2,3-d]pyrimidin-3(4H)-yl)acetamide (HSGN-0402)

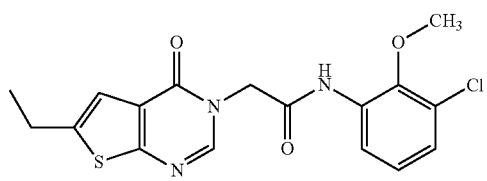 [SMILES: CCc1cc2c(=O)n(CC(=O)Nc3cccc(Cl)c3OC)cnc2s1]

¹H NMR (500 MHz, DMSO-d₆) δ 10.4 (s, 1H), 8.3 (s, 1H), 7.7 (d, J=8.2 Hz, 1H), 7.3 (d, J=8.1 Hz, 1H), 7.1 (s, 1H), 7.0 (dd, J=8.1, 2.1 Hz, 1H), 4.8 (s, 2H), 3.8 (s, 3H), 2.9-2.8 (m, 2H), 1.3 (t, J=7.5 Hz, 3H).

N-(2-cyclopropylphenyl)-2-(6-ethyl-4-oxothieno[2,3-d]pyrimidin-3(4H)-yl)acetamide (HSGN-0403)

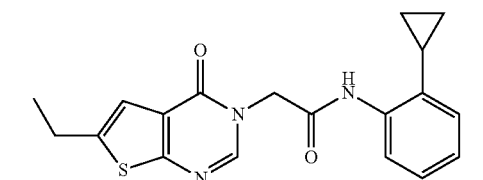

¹H NMR (500 MHz, DMSO-d₆) δ 10.2 (s, 1H), 8.3 (s, 1H), 7.4 (d, J=8.9 Hz, 1H), 7.3 (d, J=8.1 Hz, 1H), 7.2 (dd, J=8.9, 2.7 Hz, 1H), 7.1 (s, 1H), 6.9 (dd, J=8.1, 2.1 Hz, 1H), 4.8 (s, 2H), 2.9-2.8 (m, 2H), 1.9-1.7 (m, 1H), 1.6-1.4 (m, 4H), 1.3 (t, J=7.5 Hz, 3H).

N-(3-chloro-2-(methylthio)phenyl)-2-(6-ethyl-4-oxothieno[2,3-d]pyrimidin-3(4H)-yl)acetamide (HSGN-0404)

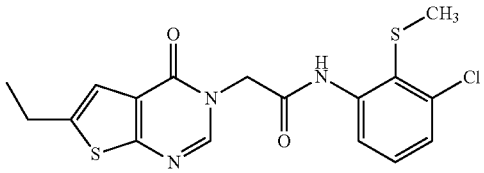 [SMILES: CCc1cc2c(=O)n(CC(=O)Nc3cccc(Cl)c3SC)cnc2s1]

$^1$H NMR (500 MHz, DMSO-d$_6$) δ 10.1 (s, 1H), 8.3 (s, 1H), 7.7 (s, 1H), 7.2 (d, J=8.2 Hz, 1H), 7.1 (s, 1H), 6.8 (d, J=8.1, 1H), 4.8 (s, 2H), 2.9-2.8 (m, 2H), 2.5 (s, 3H), 1.3 (t, J=7.5 Hz, 3H).

2-(6-ethyl-4-oxothieno[2,3-d]pyrimidin-3(4H)-yl)-N-(2-(methylthio)phenyl)acetamide (HSGN-0405)

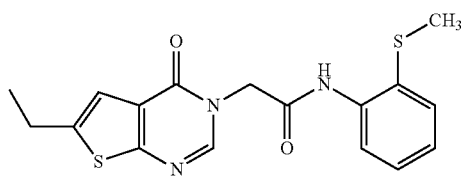 [SMILES: CCc1cc2c(=O)n(CC(=O)Nc3ccccc3SC)cnc2s1]

$^1$H NMR (500 MHz, DMSO-d$_6$) δ 10.3 (s, 1H), 8.3 (s, 1H), 7.3 (d, J=8.3 Hz, 1H), 7.2 (dd, J=8.2, 2.1 Hz, 1H), 7.1 (s, 1H), 7.0-6.9 (m, 1H), 4.8 (s, 2H), 2.9-2.8 (m, 2H), 2.4 (s, 3H), 1.3 (t, J=7.5 Hz, 3H).

2-(6-ethyl-4-oxothieno[2,3-d]pyrimidin-3(4H)-yl)-N-(4-(methylthio)phenyl)acetamide (HSGN-0406)

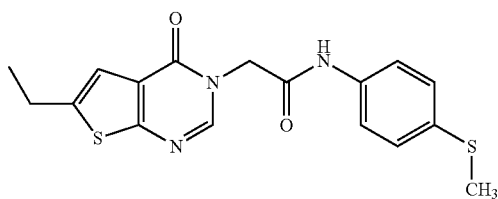 [SMILES: CCc1cc2c(=O)n(CC(=O)Nc3ccc(SC)cc3)cnc2s1]

$^1$H NMR (500 MHz, DMSO-d$_6$) δ 10.4 (s, 1H), 8.3 (s, 1H), 8.1 (d, J=8.9 Hz, 2H), 7.6 (d, J=8.9 Hz, 2H), 7.1 (s, 1H), 4.8 (s, 2H), 2.9-2.8 (m, 2H), 2.4 (s, 3H), 1.3 (t, J=7.5 Hz, 3H).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

CITED REFERENCES 1. (a) Kalia, D.; Merey, G.; Nakayama, S.; Zheng, Y.; Zhou, J.; Luo, Y.; Guo, M.; Roembke, B. T.; Sintim, H. O., Nucleotide, c-di-GMP, c-di-AMP, cGMP, cAMP, (p)ppGpp signaling in bacteria and implications in pathogenesis. Chem. Soc. Rev. 2013, 42 (1), 305-341; (b) Fahmi, T.; Port, G. C.; Cho, K. H., c-di-AMP: An Essential Molecule in the Signaling Pathways that Regulate the Viability and Virulence of Gram-Positive Bacteria. Genes 2017, 8 (8), 197; (c) Davies, Bryan W.; Bogard, Ryan W.; Young, Travis S.; Mekalanos, John J., Coordinated Regulation of Accessory Genetic Elements Produces Cyclic Di-Nucleotides for V. cholerae Virulence. Cell 2012, 149 (2), 358-370.
2. (a) Diner, Elie J.; Burdette, Dara L.; Wilson, Stephen C.; Monroe, Kathryn M.; Kellenberger, Colleen A.; Hyodo, M.; Hayakawa, Y.; Hammond, Ming C.; Vance, Russell E., The Innate Immune DNA Sensor cGAS Produces a Noncanonical Cyclic Dinucleotide that Activates Human STING. Cell Reports 2013, 3 (5), 1355-1361; (b) Ablasser, A.; Goldeck, M.; Cavlar, T.; Deimling, T.; Witte, G.; Röhl, I.; Hopfner, K.-P.; Ludwig, J.; Hornung, V., cGAS produces a 2'-5'-linked cyclic dinucleotide second messenger that activates STING. Nature 2013, 498 (7454), 380-384.
3. Sun, L.; Wu, J.; Du, F.; Chen, X.; Chen, Z. J., Cyclic GMP-AMP Synthase Is a Cytosolic DNA Sensor That Activates the Type I Interferon Pathway. Science 2013, 339 (6121), 786.
4. Danilchanka, O.; Mekalanos, John J., Cyclic Dinucleotides and the Innate Immune Response. Cell 2013, 154 (5), 962-970.
5. (a) Sambanthamoorthy, K.; Sloup, R. E.; Parashar, V.; Smith, J. M.; Kim, E. E.; Semmelhack, M. F.; Neiditch, M. B.; Waters, C. M., Identification of Small Molecules That Antagonize Diguanylate Cyclase Enzymes To Inhibit Biofilm Formation. Antimicrob. Agents Chemother. 2012, 56 (10), 5202-5211; (b) Lieberman, O. J.; Orr, M. W.; Wang, Y.; Lee, V. T., High-Throughput Screening Using the Differential Radial Capillary Action of Ligand Assay Identifies Ebselen As an Inhibitor of Diguanylate Cyclases. ACS Chem. Biol. 2014, 9 (1), 183-192; (c) Sambanthamoorthy, K.; Luo, C.; Pattabiraman, N.; Feng, X.; Koestler, B.; Waters, C. M.; Palys, T. J., Identification of small molecules inhibiting diguanylate cyclases to control bacterial biofilm development. Biofouling 2014, 30 (1), 17-28.
6. (a) Zheng, Y.; Zhou, J.; Sayre, D. A.; Sintim, H. O., Identification of bromophenol thiohydantoin as an inhibitor of DisA, a c-di-AMP synthase, from a 1000 compound library, using the coralyne assay. Chem. Commun. 2014, 50 (76), 11234-11237; (b) Opoku-Temeng, C.; Sintim, H. O., Potent inhibition of cyclic diadenylate monophosphate cyclase by the antiparasitic drug, suramin. Chem. Commun. 2016, 52 (19), 3754-3757; (c) Opoku-Temeng, C.; Sintim, H. O., Inhibition of cyclic diadenylate cyclase, DisA, by polyphenols. *Sci. Rep.* 2016, 6, 25445-25445.
7. Opoku-Temeng, C.; Dayal, N.; Miller, J.; Sintim, H. O., Hydroxybenzylidene-indolinones, c-di-AMP synthase inhibitors, have antibacterial and anti-biofilm activities and also re-sensitize resistant bacteria to methicillin and vancomycin. *RSC Advances* 2017, 7 (14), 8288-8294.
8. Kawaguchi, M.; Han, X.; Hisada, T.; Nishikawa, S.; Kano, K.; Ieda, N.; Aoki, J.; Toyama, T.; Nakagawa, H., Development of an ENPP1 Fluorescence Probe for Inhibitor Screening, Cellular Imaging, and Prognostic Assessment of Malignant Breast Cancer. *J. Med. Chem.* 2019, 62 (20), 9254-9269.
9. Corrigan, R. M.; Campeotto, I.; Jeganathan, T.; Roelofs, K. G.; Lee, V. T.; Gründling, A., Systematic identification of conserved bacterial c-di-AMP receptor proteins. *Proc. Natl. Acad. Sci. U.S.A.* 2013, 110 (22), 9084-9089.
10. (a) Dey, R. J.; Dey, B.; Zheng, Y.; Cheung, L. S.; Zhou, J.; Sayre, D.; Kumar, P.; Guo, H.; Lamichhane, G.; Sintim, H. O.; Bishai, W. R., Inhibition of innate immune cytosolic surveillance by an *M. tuberculosis* phosphodiesterase. *Nat. Chem. Biol.* 2017, 13 (2), 210-217; (b) Andrade, Warrison A.; Firon, A.; Schmidt, T.; Hornung, V.; Fitzgerald, Katherine A.; Kurt-Jones, Evelyn A.; Trieu-Cuot, P.; Golenbock, Douglas T.; Kaminski, P.-A., Group B *Streptococcus* Degrades Cyclic-di-AMP to Modulate STING-Dependent Type I Interferon Production. *Cell Host Microbe* 2016, 20 (1), 49-59; (c) Quach, D.; van Sorge, N. M.; Kristian, S. A.; Bryan, J. D.; Shelver, D. W.; Doran, K. S., The CiaR Response Regulator in Group B *Streptococcus* Promotes Intracellular Survival and Resistance to Innate Immune Defenses. *J. Bacteriol.* 2009, 191 (7), 2023.
11. Eaglesham, J. B.; Pan, Y.; Kupper, T. S.; Kranzusch, P. J., Viral and metazoan poxins are cGAMP-specific nucleases that restrict cGAS-STING signalling. *Nature* 2019, 566 (7743), 259-263.
12. de Cheffoy de Courcelles, D.; de Loore, K.; Freyne, E.; Janssen, P. A., Inhibition of human cardiac cyclic AMP-phosphodiesterases by R 80122, a new selective cyclic AMP-phosphodiesterase III inhibitor: a comparison with other cardiotonic compounds. *J. Pharmacol. Exper. Ther.* 1992, 263 (1), 6.
13. Man, H.-W.; Schafer, P.; Wong, L. M.; Patterson, R. T.; Corral, L. G.; Raymon, H.; Blease, K.; Leisten, J.; Shirley, M. A.; Tang, Y.; Babusis, D. M.; Chen, R.; Stirling, D.; Muller, G. W., Discovery of (S)—N-{2-[1-(3-Ethoxy-4-methoxyphenyl)-2-methanesulfonylethyl]-1,3-dioxo-2,3-dihydro-1H-isoindol-4-yl}acetamide (Apremilast), a Potent and Orally Active Phosphodiesterase 4 and Tumor Necrosis Factor-α Inhibitor. *J. Med. Chem.* 2009, 52 (6), 1522-1524.
14. Wang, Z.; Zhu, D.; Yang, X.; Li, J.; Jiang, X.; Tian, G.; Terrett, N. K.; Jin, J.; Wu, H.; He, Q.; Yang, B.; Shen, J., The selectivity and potency of the new PDE5 inhibitor TPN729MA. *J. Sex. Med.* 2013, 10 (11), 2790-7.
15. Grauer, S. M.; Pulito, V. L.; Navarra, R. L.; Kelly, M. P.; Kelley, C.; Graf, R.; Langen, B.; Logue, S.; Brennan, J.; Jiang, L.; Charych, E.; Egerland, U.; Liu, F.; Marquis, K. L.; Malamas, M.; Hage, T.; Comery, T. A.; Brandon, N. J., Phosphodiesterase 10A Inhibitor Activity in Preclinical Models of the Positive, Cognitive, and Negative Symptoms of Schizophrenia. *J. Pharmacol. Exper. Ther.* 2009, 331 (2), 574.
16. (a) Zheng, Y.; Tsuji, G.; Opoku-Temeng, C.; Sintim, H. O., Inhibition of *P. aeruginosa* c-di-GMP phosphodiesterase RocR and swarming motility by a benzoisothiazolinone derivative. *Chem. Sci.* 2016, 7 (9), 6238-6244; (b) *Microbial Cyclic Di-Nucleotide Signaling.* Springer: ebook, 2020.
17. Zhou, J.; Sayre, D. A.; Zheng, Y.; Szmacinski, H.; Sintim, H. O., Unexpected Complex Formation between Coralyne and Cyclic Diadenosine Monophosphate Providing a Simple Fluorescent Turn-on Assay to Detect This Bacterial Second Messenger. *Anal. Chem.* 2014, 86 (5), 2412-2420.
18. Zhang, J.-H.; Chung, T. D. Y.; Oldenburg, K. R., A Simple Statistical Parameter for Use in Evaluation and Validation of High Throughput Screening Assays. *J. Biomol. Screen.* 1999, 4 (2), 67-73.
19. Dey, R. J.; Dey, B.; Zheng, Y.; Cheung, L. S.; Zhou, J.; Sayre, D.; Kumar, P.; Guo, H.; Lamichhane, G.; Sintim, H. O.; Bishai, W. R., Inhibition of innate immune cytosolic surveillance by an *M. tuberculosis* phosphodiesterase. *Nat. Chem. Biol.* 2016, 13, 210.
20. Yammine, A.; Gao, J.; Kwan, A. H., Tryptophan Fluorescence Quenching Assays for Measuring Protein-ligand Binding Affinities: Principles and a Practical Guide. *Bio-protocol* 2019, 9 (11), e3253.
21. Rao, F.; See, R. Y.; Zhang, D.; Toh, D. C.; Ji, Q.; Liang, Z.-X., YybT Is a Signaling Protein That Contains a Cyclic Dinucleotide Phosphodiesterase Domain and a GGDEF Domain with ATPase Activity. *J. Biol. Chem.* 2010, 285 (1), 473-482.
22. (a) Kulesekara, H.; Lee, V.; Brencic, A.; Liberati, N.; Urbach, J.; Miyata, S.; Lee, D. G.; Neely, A. N.; Hyodo, M.; Hayakawa, Y.; Ausubel, F. M.; Lory, S., Analysis of *Pseudomonas aeruginosa* diguanylate cyclases and phosphodiesterases reveals a role for bis-(3'-5')-cyclic-GMP in virulence. *Proc. Natl. Acad. Sci. U.S.A.* 2006, 103 (8), 2839-2844; (b) Andrade, Warrison A.; Firon, A.; Schmidt, T.; Hornung, V.; Fitzgerald, Katherine A.; Kurt-Jones, Evelyn A.; Trieu-Cuot, P.; Golenbock, Douglas T.; Kaminski, P.-A., Group B *Streptococcus* Degrades Cyclic-di-AMP to Modulate STING-Dependent Type I Interferon Production. *Cell Host Microbe* 2016, 20 (1), 49-59.
23. Rao, F.; See, R. Y.; Zhang, D.; Toh, D. C.; Ji, Q.; Liang, Z.-X., YybT is a signaling protein that contains a cyclic dinucleotide phosphodiesterase domain and a GGDEF domain with ATPase activity. *J. Biol. Chem.* 2010, 285 (1), 473-482.
24. Rao, F.; Yang, Y.; Qi, Y.; Liang, Z.-X., Catalytic Mechanism of Cyclic Di-GMP-Specific Phosphodiesterase: a Study of the EAL Domain-Containing RocR from *Pseudomonas aeruginosa. J. Bacteriol.* 2008, 190 (10), 3622.
25. Ines Baronel, Cinzia Giordano2, Daniela Bonofigliol, Sebastiano Andòl and Stefania Catalano1, Phosphodiesterase type 5 and cancers: progress and challenges. *Oncotarget,* 2017, Vol. 8, (No. 58), pp: 99179-99202.

We claim:
1. A compound of a generic structure,

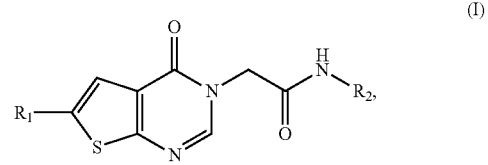

or a pharmaceutically acceptable salt thereof, wherein

R₁ is a 1-6 alkyl, or 6-14 aryl, which is optionally substituted; and

R₂ is a cycloalkyl, or aryl, each of which is optionally substituted.

2. The compound of claim 1, wherein said compound has a generic structure of

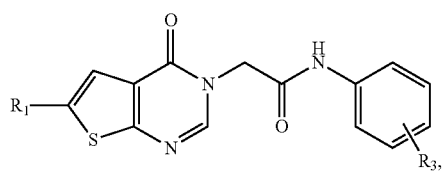

(II)

wherein

R₁ is a hydrogen, 1-6 alkyl, 6-14 aryl, each of which is optionally substituted; and R₃ represents five substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety.

3. The compound of claim 1, wherein said compound has a formular of

HSGN-0401

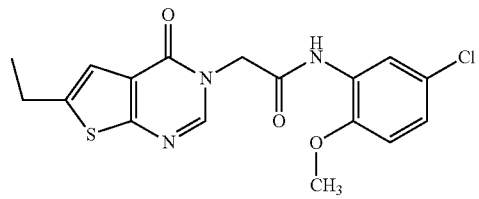

HSGN-0402

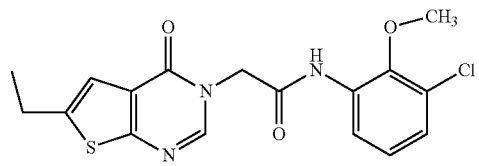

HSGN-0403

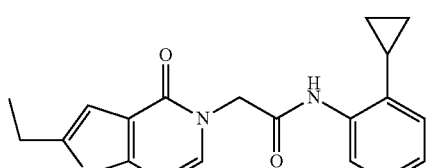

HSGN-0404

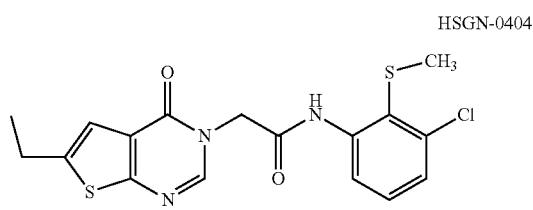

HSGN-0405

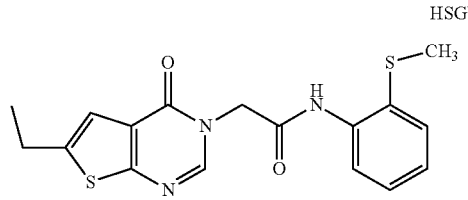

HSGN-0406

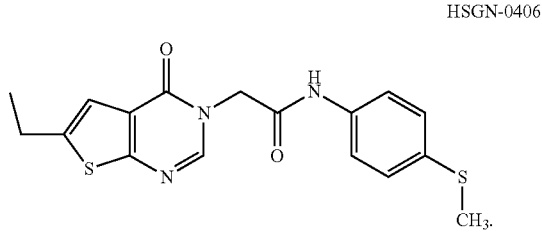

4. The compound of claim 1, wherein said compound is an inhibitor for cyclic mononucleotide or cyclic dinucleotide PDE.

5. A pharmaceutical composition comprising one or more compounds of claim 1, together with one or more pharmaceutically acceptable carriers or diluents.

6. A compound of claim 1, wherein said compound is acid sensitive or reactive to an enzyme.

* * * * *